(12) United States Patent
Matsui et al.

(10) Patent No.: US 6,352,503 B1
(45) Date of Patent: Mar. 5, 2002

(54) ENDOSCOPIC SURGERY APPARATUS

(75) Inventors: Raifu Matsui, Hino; Ryuta Sekine, Chofu; Keiichi Arai, Hachioji, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/354,011

(22) Filed: Jul. 15, 1999

(30) Foreign Application Priority Data

Jul. 17, 1998 (JP) .......................................... 10-203479
Jul. 21, 1998 (JP) .......................................... 10-205101

(51) Int. Cl.$^7$ ................................................. A61B 1/00
(52) U.S. Cl. ........................ 600/104; 600/106; 600/107
(58) Field of Search ................................ 600/104–107, 600/153

(56) References Cited

U.S. PATENT DOCUMENTS 3,915,157 A  * 10/1975 Mitsui ........................ 600/107

FOREIGN PATENT DOCUMENTS

| JP | 54-136780 | | 10/1979 | | |
| JP | 405184534 A | * | 7/1993 | ............ | A61B/1/00 |
| JP | 409262239 | * | 10/1997 | .................. | 600/104 |

* cited by examiner

Primary Examiner—John Mulcahy
(74) Attorney, Agent, or Firm—Frishauf, Holtz, Goodman, Langer & Chick, P.C.

(57) ABSTRACT

The present invention is directed to an endoscopic surgery apparatus for performing treating operation in a body cavity of a patient with the use of treating tools in combination with an endoscope, in which insertion sections allowing the insertion of treating tools are externally arranged in a side-by-side fashion with an insertion section of the endoscope set between these insertion sections and a balloon is provided near a distal end of the insertion section of the endoscope to adjust a relative distance between the insertion sections relative to the insertion section of the endoscope. The balloon is provided on the insertion section of the endoscope and, when the endoscope and treating tools are introduced into the body cavity of the patient, it is possible to easily and properly lead the endoscope and treating tools to a region of interest of the patient.

16 Claims, 16 Drawing Sheets

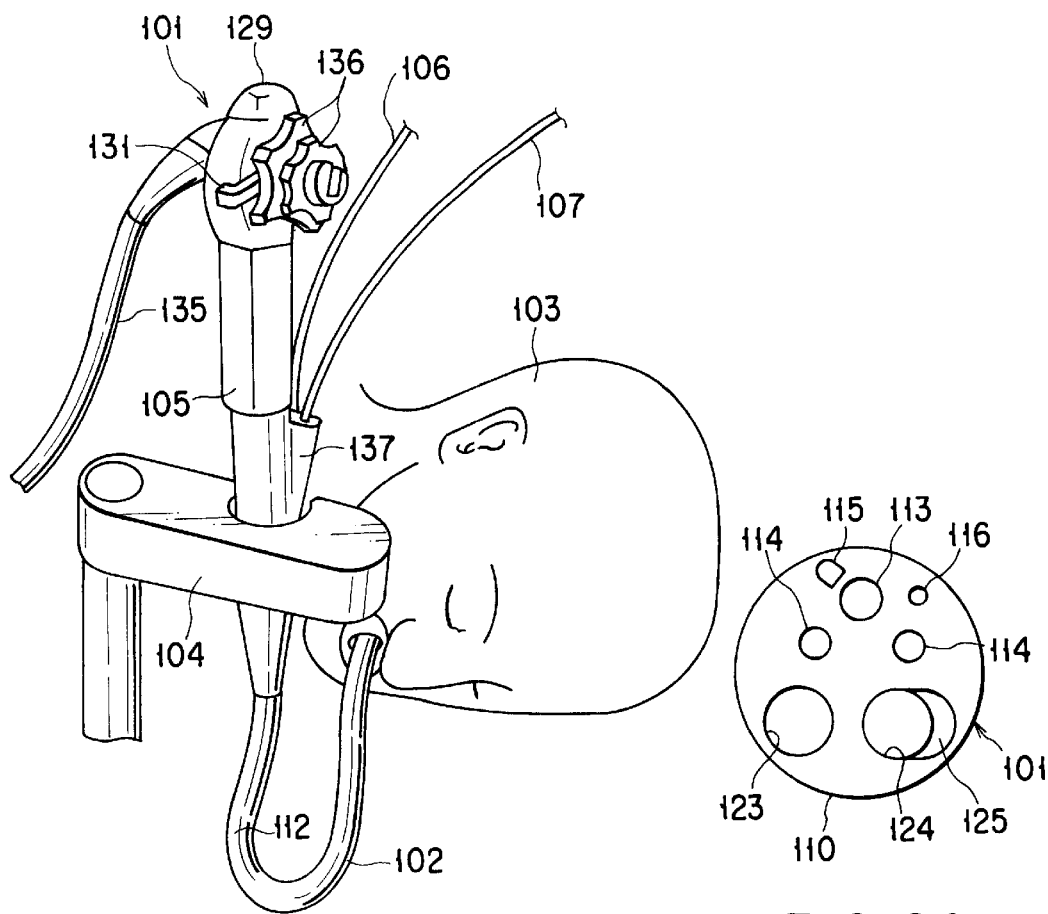
FIG. 22
FIG. 24
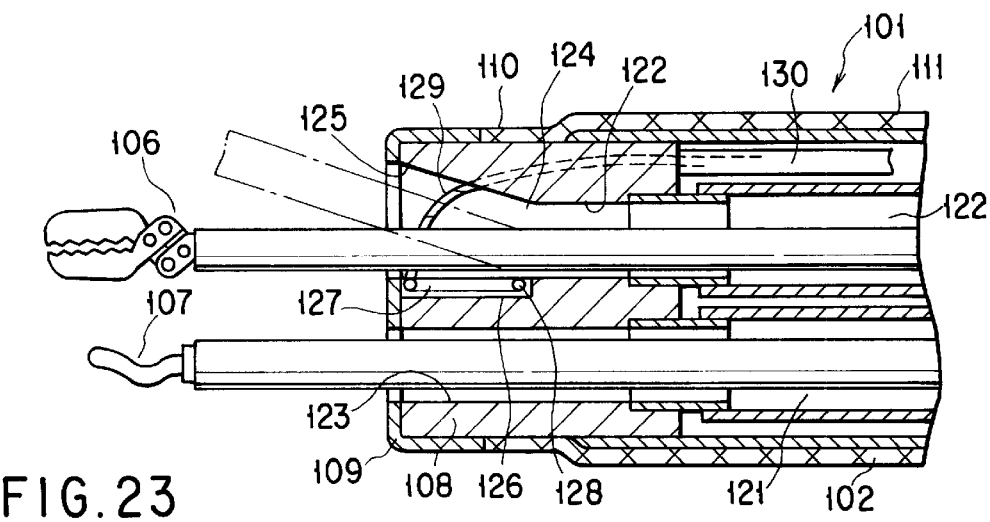
FIG. 23

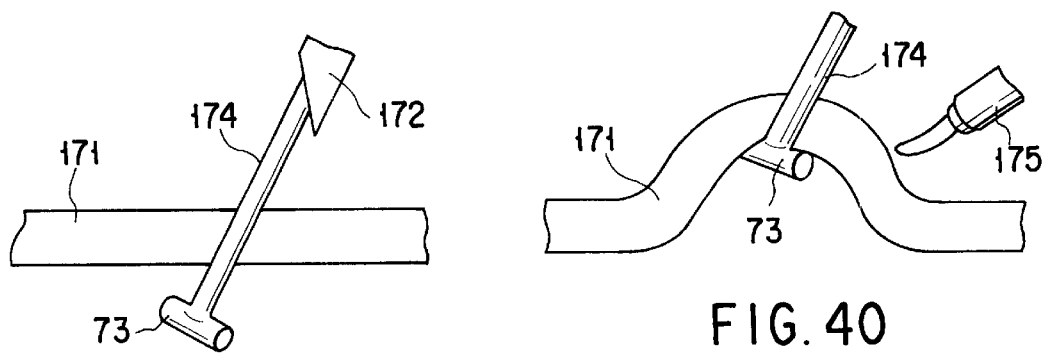
FIG. 39
FIG. 40
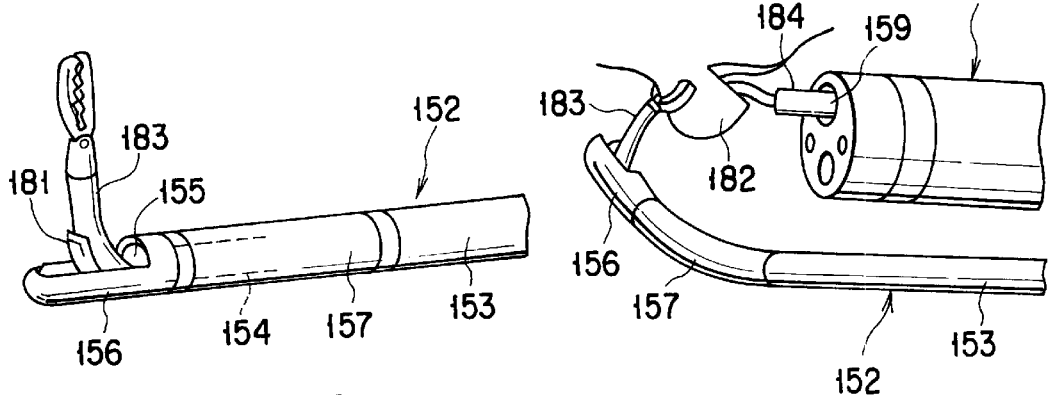
FIG. 41
FIG. 42
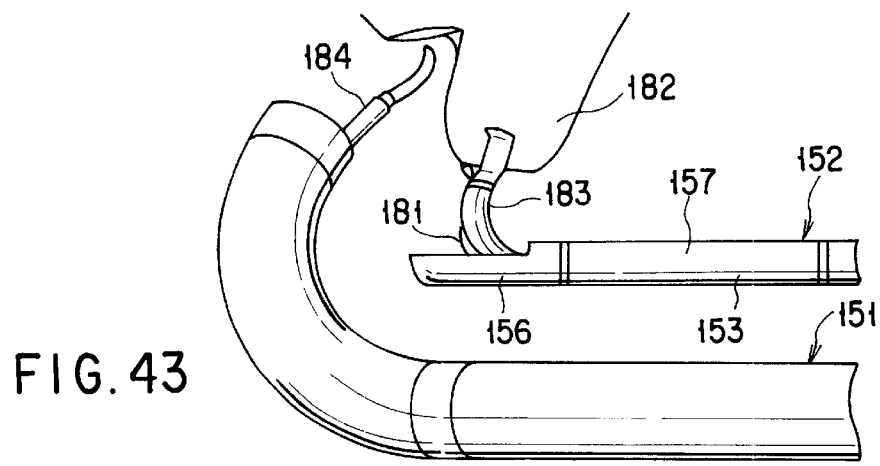
FIG. 43

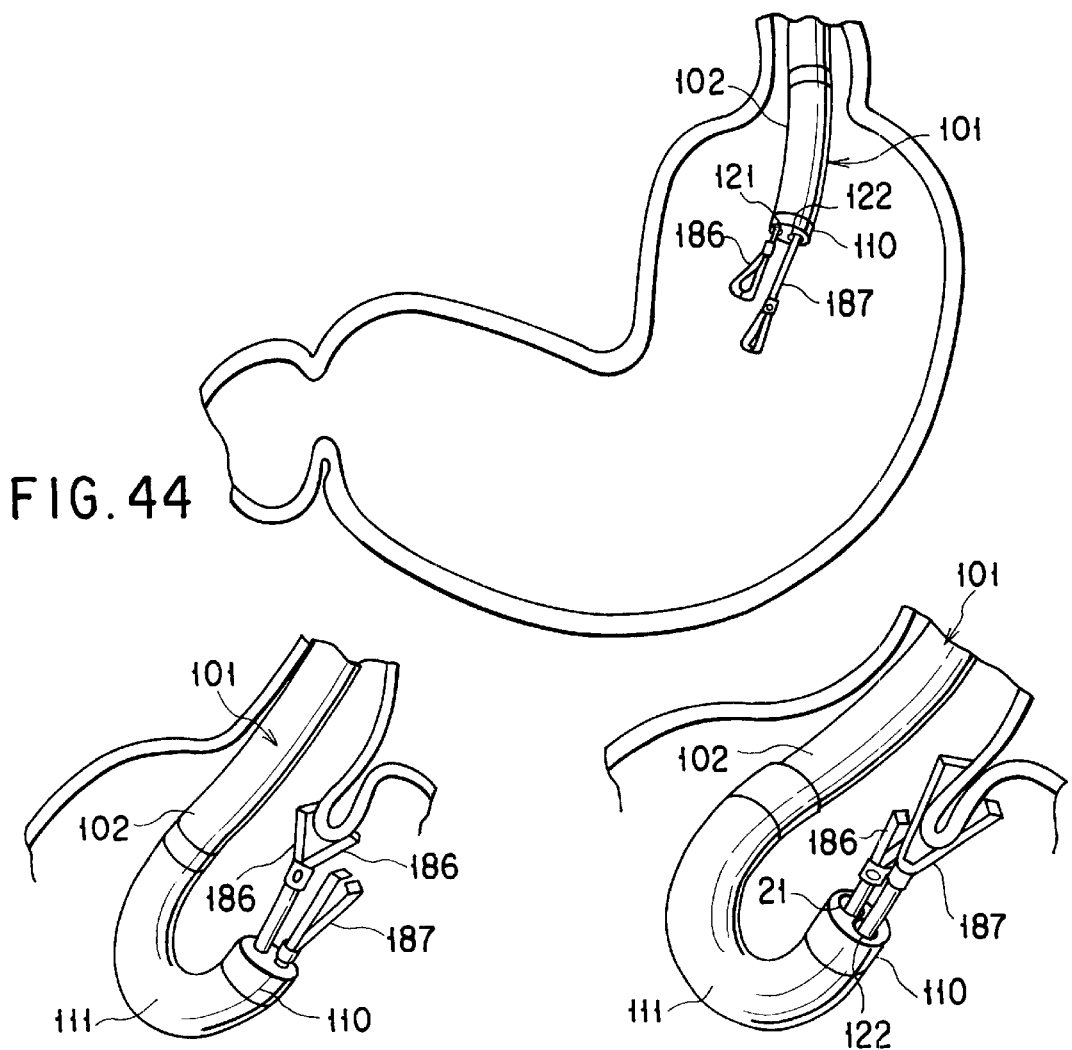
FIG. 44
FIG. 45
FIG. 46
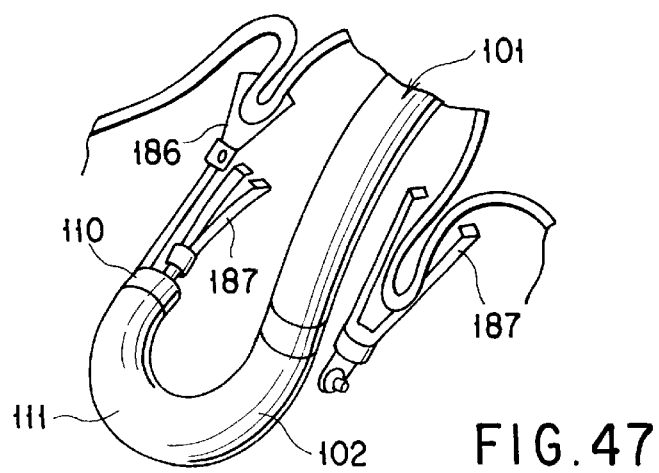
FIG. 47

ENDOSCOPIC SURGERY APPARATUS

BACKGROUND OF THE INVENTION

The present invention relates to an endoscopic surgery apparatus for performing treating operation on a region of interest in a body cavity of a patient by using an endoscope having an insertion section inserted into the body cavity in combination with the treating tools.

The treating procedure for performing treating operation on a region of interest in the body cavity of a patient has been conventionally carried out by using treating tools in connection with the endoscope. JPN PAT APPLN KOKAI PUBLICATION NO. 54-136780 discloses the surgery technology as will be set out below. That is, an insertion guide tool having a plurality of passageways is inserted into the body cavity of the patient and an endoscope and treating tools are individually inserted into the passageways. And the insertion section of the endoscope and insertion section of the treating tool are introduced into the body cavity of the patient and, in the body cavity of the patient, the insertion section of the endoscope and insertion section of the treating tool are led to a diseased region from a different direction and, by doing so, treatment is performed on the diseased region.

According to the conventional technique of the KOKAI, a relative position between the insertion section of the endoscope and the insertion section of the treating tool in the body cavity of the patient is set and both the insertion section of the endoscope and the insertion section of the treating tool are readily led to the diseased region.

Since, however, the insertion section of the endoscope and insertion section of the treating tool are separately introduced into the cavity of the patient past the associated passageways in the insertion guide tool, these insertion sections of the endoscope and treating tool are brought close to each other, so that a relative positional relation is likely to be restricted to a narrow range. If, for example, the insertion sections of the endoscope and treating tool are set to a diseased region in the stomach, then their relative position is improperly displaced. And there has been some inconvenience of encountering difficulty, in the proper treatment of a diseased region, such as the cutting off of the diseased region.

BRIEF SUMMARY OF THE INVENTION

It is accordingly the object of the present invention to provide an endoscopic surgery apparatus which can lead an endoscope and treating means or the treating means to a diseased region properly and readily and positively perform treatment on the diseased region.

The above-mentioned object of the present invention can be achieved by the invention as will be set out. That is, the present invention provides an endoscopic surgery apparatus for performing treatment operation on a diseased region in a body cavity of a patient by using an endoscope inserted into the body cavity of the patient and having an insertion section with at least an observation system, that is, using treating tools in combination with the endoscope, the apparatus comprising an observation device having the endoscope; first and second treating tools used in combination with the endoscope and having an insertion section; a distance adjusting device for adjusting a relative distance between at least one pair of an insertion section of the endoscope, an insertion section of the first treating tool, and an insertion section of the second treating tool in a direction substantially orthogonal with an axial direction of the insertion section of the endoscope; and an operation device for remotely operating the distance adjusting device.

According to the endoscopic surgery apparatus, it is possible to readily and positively perform treatment operation by leading an insertion section of the endoscope serving as an observation means and insertion sections of treating means having, for example, a different treating function or a plurality of treating functions to a diseased region from a different direction.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 22 is a perspective view conceptually showing a situation under which a seventh embodiment is used;

FIG. 23 is a cross-sectional view showing a distal end, and its neighborhood, of an insertion section of an endoscope according to the seventh embodiment;

FIG. 24 is a front view showing a front end face of the distal end of the insertion section of the endoscope according to the seventh embodiment;

FIG. 39 is an explanatory view showing a situation under which treating operation is performed on the living tissue portion by the treating endoscope;

FIG. 40 is an explanatory view showing a situation under which treating operation is performed on the living tissue by the treating endoscope;

FIG. 41 is a perspective view showing another form of treating tool insertion tool;

FIG. 42 is an explanatory view showing a situation under which treating operation is performed on the living tissue portion by the treating tool insertion tool;

FIG. 43 is an explanatory view showing a situation under which treating operation is performed on the living tissue portion by the treating tool insertion tool;

FIG. 44 is an explanatory view showing a situation under which treating operation is performed by still another treating endoscope;

FIG. 45 is an explanatory view showing a situation under which treating operation is performed on a living tissue portion by the treating endoscope;

FIG. 46 is an explanatory view showing a situation under which treating operation is performed on the living tissue portion by the treating endoscope;

FIG. 47 is an explanatory view showing a situation under which treating operation is performed on a living tissue portion by the treating endoscope;

DETAILED DESCRIPTION OF THE INVENTION (First Embodiment)

A first embodiment of the present invention will be explained below with reference to FIGS. 1 to 12.

Figure 1:
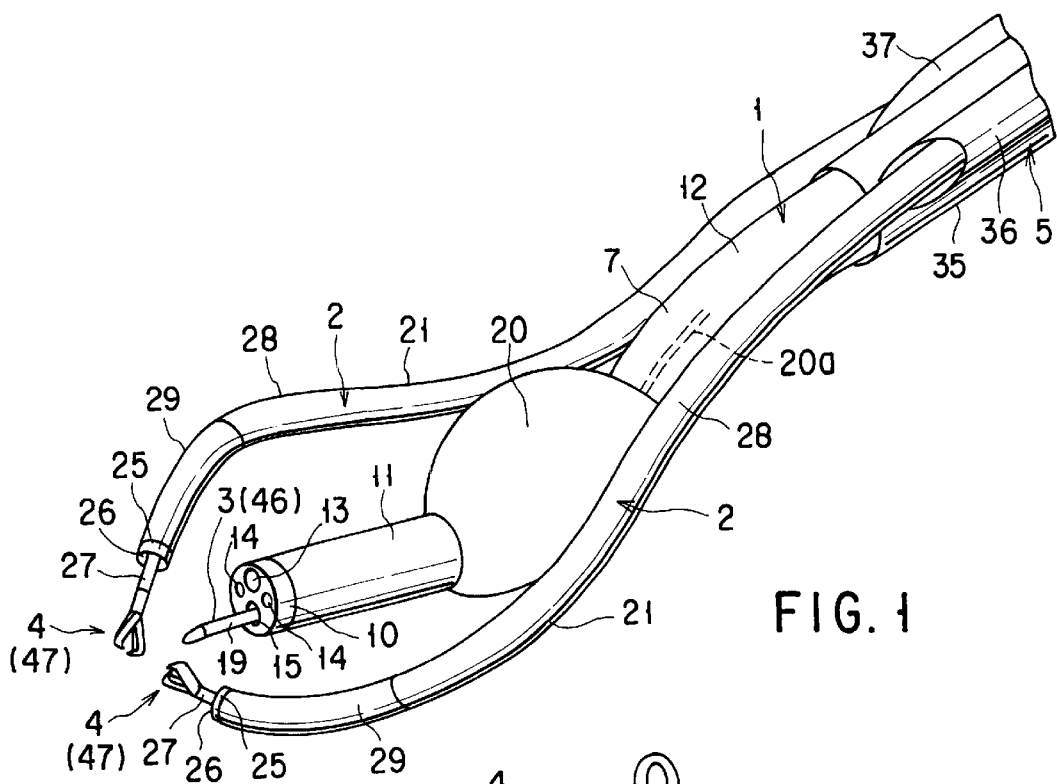
FIG. 1 is a perspective view showing a distal end side section of an endoscopic surgery apparatus according to a first embodiment.
Figure 2:
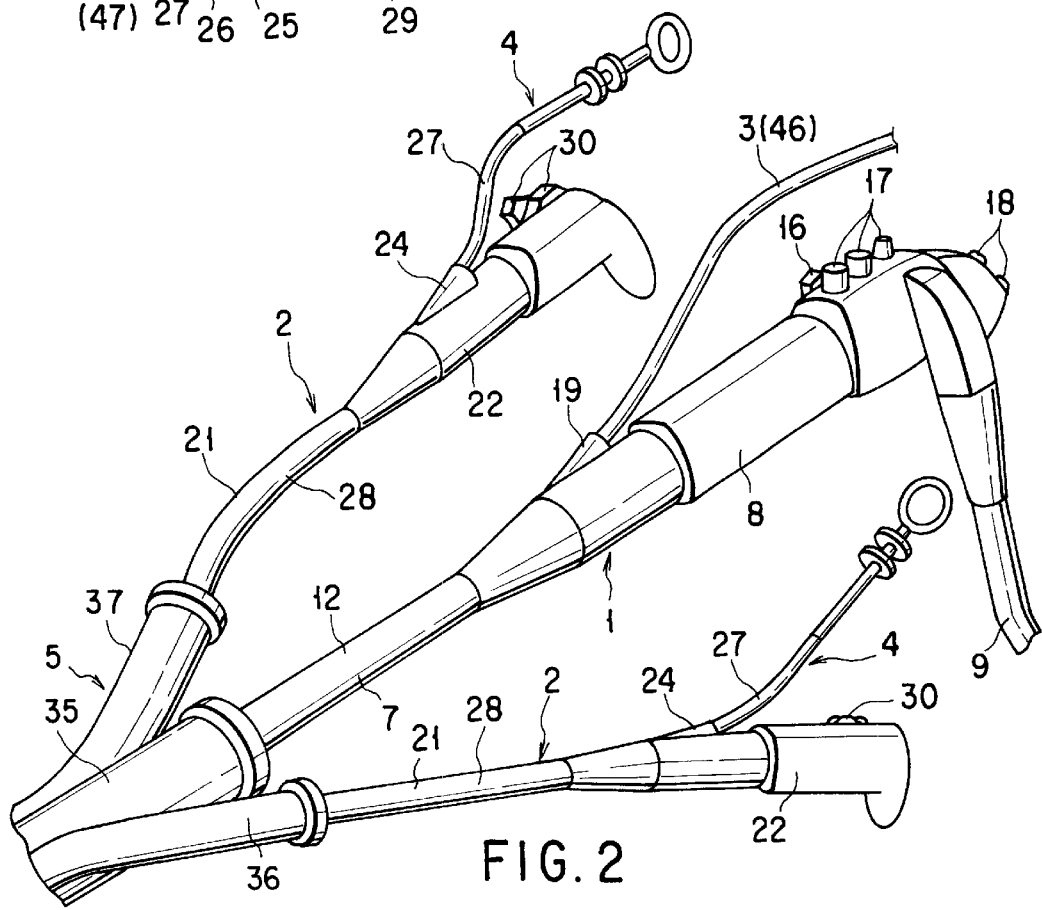
FIG. 2 is a perspective view showing a proximal end side section of the endoscopic surgery apparatus in use.

FIGS. 1 and 2 are perspective views showing an endoscopic surgery apparatus, FIG. 1 showing distal end portions of respective associated tools and FIG. 2 showing proximal end portion of the associated tools. The endoscopic surgery apparatus comprises an endoscope 1, two treating tool leading insertion tools (guide tubes) 2, treating tools 3, 4, and an outer (over) tube unit 5 serving as an introduction guide unit equipped with three-part tube section for leading insertion sections of the endoscope 1 and two treating tool leading insertion tools 2 individually to a body cavity of a human subject.

The endoscope 1 has a flexible insertion section 7 and proximal operation section 8. A light source device, not shown, and universal cord 9 are connected to a proximal operation section 8, the universal cord being connected to a video processor, not shown.

A body of the endoscope 1 contains an observation optical system, illumination optical system, channels, etc. The insertion section 7 comprises a distal end section 10, a bending section 11 adjacent the distal end section and a flexible tube 12 connected to the proximal end side of the bending section 11 and is formed as a lengthy member. An observation window 13 of the observation optical system, illumination window 14 of the illumination optical system and distal end opening 15 of the channel are provided at the distal end section 10. The bending section 11 is provided on a mid-way at the forward end side of the insertion section 7 and adapted to be bent by the operation of an angle knob 16 on the proximal operation section 8.

The proximal operation section 8 has various operation buttons 17 or various kinds of switch operation buttons 18 which allow a supply of air, supply of water, a suction or a switching operation such as a supply of fluid to and from a balloon to be later described.

The proximal operation section 8 is equipped with a treating tool insertion inlet 19 leading to the channel. The treating tool 3 is inserted via the treating tool insertion inlet 19 and the distal end of the treating tool 3 is projected out of the distal end opening 15 past the channel. The endoscope 1, though being omitted in illustration, is incorporated in the present embodiment and is of such a type as to include a conventional structure for use in the washing of an observation lens and supply of air through the nozzle.

A means for adjusting a relative distance of it to another tool is provided near the distal end of the insertion section 7 of the endoscope. Here, as the adjusting means, use is made of the balloon 20 as will be set forth in more detail below.

Figure 4:
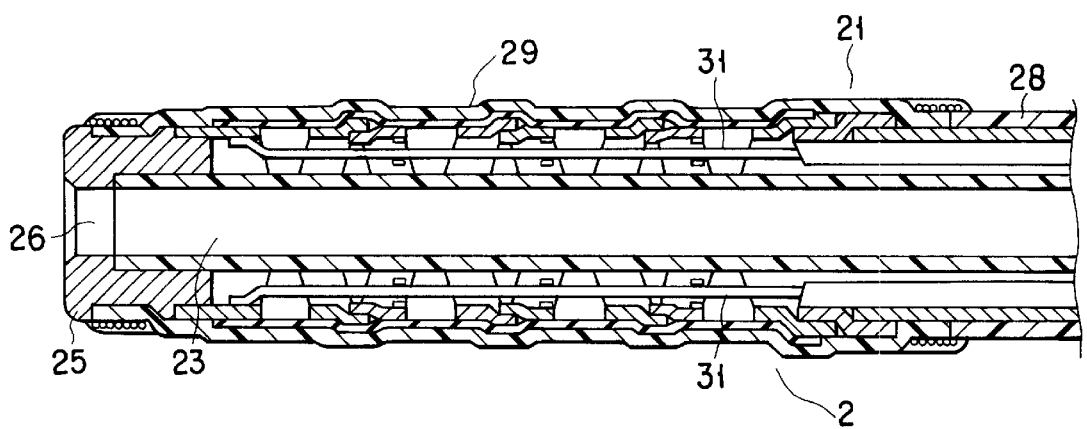
FIG. 4 is a longitudinal cross-section showing a section near a distal end of a treating tool leading insertion tool of the endoscopic surgery apparatus.

As shown in FIGS. 1 and 2, the treating tool leading insertion tool 2 has a flexible insertion section 21 and proximal operation section 22. AS shown in FIG. 4, a channel 23 is created in the insertion section 21 to allow the treating tool 4 to pass therethrough. The channel 23 is formed which extends from a treating tool insertion inlet 21 at a proximal operation section 22 to a distal end opening 26 opened at a distal end face of the distal end section 25 of the insertion section 21 as shown in FIG. 2. The insertion section 27 of the treating tool 4 is inserted from a treating tool insertion section 24 into the channel 23 and is projected out of the distal end opening 26 after passing through the channel 23.

The insertion section 21 of the treating tool leading insertion tool 2 comprises a flexible tube 28, a bending section 29 connected to the distal end of the tube 28 and the above-mentioned distal end section 25.

The above-mentioned bending section 29 is bendable, as in the case of an ordinary endoscope, by pushing/pulling an operation wire 31 by an angle knob 30 at a proximal operation section 22 though the insertion section 21 (see FIG. 4). Here, the treating tool leading insertion section 2 mainly has a channel 23 to allow the treating tool 4 to be inserted from the proximal end side of the treating tool 4 into the insertion section 21 and does not possess any observation optical system, illumination optical system, other channels, etc. For this reason, the insertion section 21 of the treating tool leading insertion tool 2 has an external diameter narrower than the insertion section 7 of the endoscope 1.

The above-mentioned treating tool leading insertion tool 2 has at least an outer portion of the distal end section 25 of its insertion section 21 formed of a member of an electrically insulating resin, because use is sometimes made of a treating tool which uses a high frequency current in the channel 23 or the channel of the endoscope 1, and the treating tool leading insertion tool 2 has, therefore, such a structure as to electrically insulatively shield the above-mentioned insertion section 21 from the high frequency current used in the high frequency treating tool.

Figure 3:
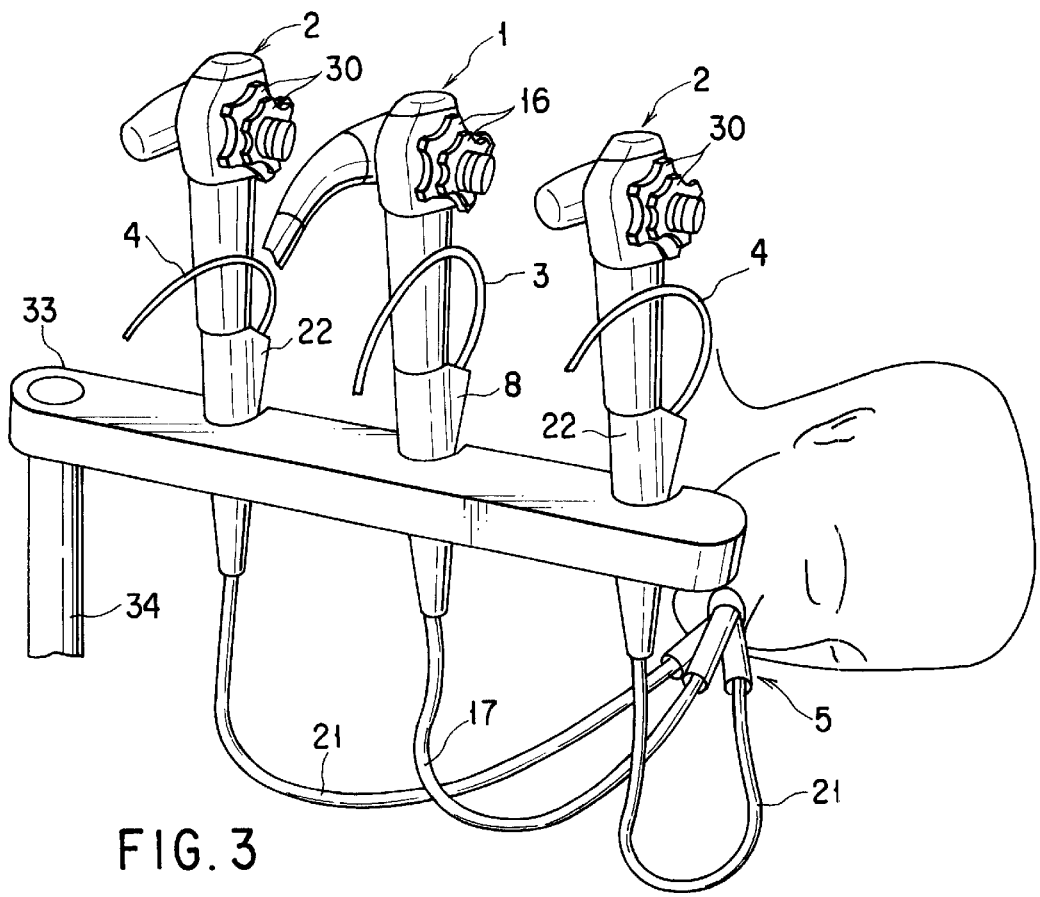
FIG. 3 is a perspective view showing the endoscopic surgery apparatus in use with the proximal end section in a held state.

FIG. 2 shows those proximal end portions of the respective associated tools in the above-mentioned endoscopic surgery apparatus. The proximal end portions are those portions operated by an operator outside the body cavity of the patient and, when being actually used, the proximal operation section 8 of the endoscope 1 and either of the proximal operation sections 22 of the two processing tool leading insertion tools 2 are held in place on an operation mount 33 as shown in FIG. 3.

Figure 5:
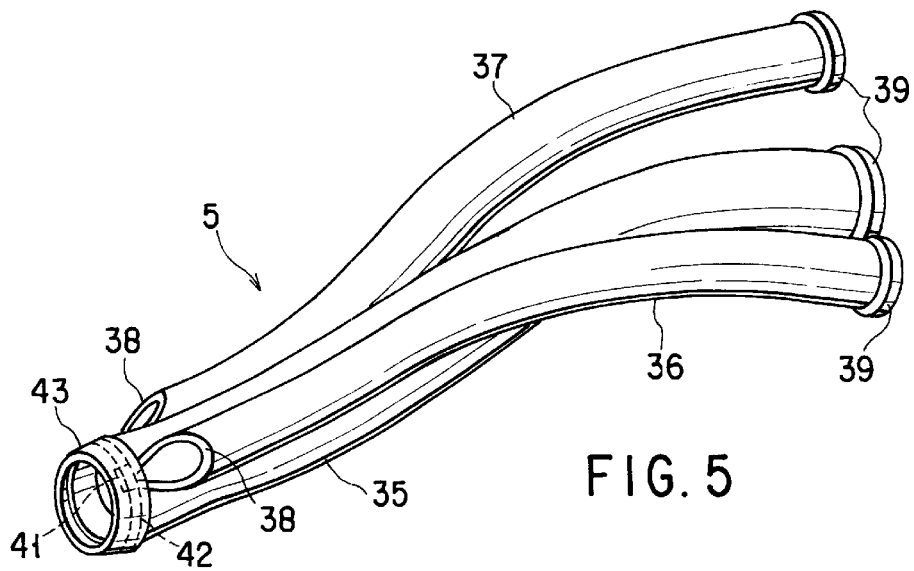
FIG. 5 is a perspective view showing an outer tube unit of the endoscopic surgery apparatus.

The outer tube unit 5 has, as shown in FIG. 5, a first tube 35 for allowing an insertion section 7 of the endoscope 1 to be passed therethrough, and second and third tubes 36 and 37 for allowing the insertion sections 21 of the two treating tool leading insertion tools 2 to pass therethrough, that is, has three tubes in total. The first tube 35 is greater in diameter than the other two tubes 36 and 37. These tubes 35, 36 and 37 are each comprised of a tube member made of a flexible material, such as urethane resin and porous fluorine resin.

Figure 6:
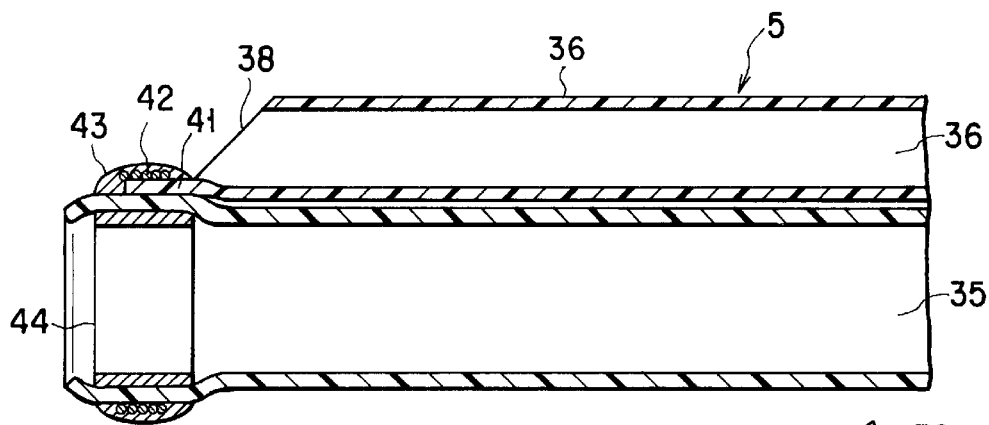
FIG. 6 is a longitudinal cross-section showing a section near a distal end of the outer tube unit of the endoscopic surgery apparatus.

As shown in FIGS. 5 and 6, these tubes 35, 36 and 37 are such that only their distal end side portions inserted into the body cavity of a patient are bundled together. In this case, the distal end portions of the second and third tubes 36 and 37 are joined and bundled on the outer peripheral surface of the distal end portion of the first tube of the largest diameter. The distal ends of the second and third tubes 36 and 37 provide end faces rearwardly inclined at an acute angle with respect to their axial directions, so that the distal open faces of the second and third tubes 36 and 37 are oriented in forwardly outwardly inclined relation.

Tongue portions 41 are provided at the distal ends of the second and third tubes 36 and 37 to allow them to be joined to the outer peripheral surface of the first tube 35. With the tongue portions 41 joined to the outer peripheral surface of the distal end portion of the first tube 35, these tongue portions 41 are tied by a string 42 and securely bundled. Further, an adhesive 43 is coated on the outer surfaces of the tongue portions 41 and strings 42 to provide a smoothly finished surface.

As shown in FIG. 6, a ring-like connector member 44 of metal or hard resin is fitted in a distal end portion of the inner bore of the first tube 35 and, by doing so, the bundled portion is reinforced and a high strength is added to the bundled portion.

As shown in FIG. 5, the proximal end side portions of the three tubes 35, 36 and 37 of the outer tube unit 5 situated outside the body cavity of the patient are independently set in a free state. Connectors 39 are provided on the proximal ends of these tubes 35, 36 and 37.

As shown in FIG. 1, the balloon 20, expandable and shrinkable, is located on the insertion section 7 of the endoscope 1 just at the back of the bending section 11 or at a place including the bending section 11. The balloon 20 is expanded and shrunk by the operation at the proximal operation section. The balloon 20 constitutes a position adjusting means which properly separates the insertion sections 21 of, for example, the treating tool leading insertion tools 2 away from each other which tend to be moved nearer each other when the balloon 20 is expanded. The position adjusting means adjusts or controls a relative position among the respective insertion sections 7 and 21 in accordance with the extent of expansion of the balloon 20.

The balloon 20 is connected to a tube 20a arranged in the interior of the insertion section 7. Through the tube 20a, a fluid such as a physiological salt solution is supplied to and from the balloon 20. The control operation by which the fluid is supplied to and from the balloon 20 is done by the use of, for example, one of the balloon operation buttons 17 at the proximal operation section 8 of the endoscope 1. The balloon 20 is expanded by supplying the fluid to the balloon and shrunk by discharging the fluid from the balloon 20. The balloon 20 can be shrunk to an extent corresponding to the external diameter of the insertion section 7.

Figure 7:
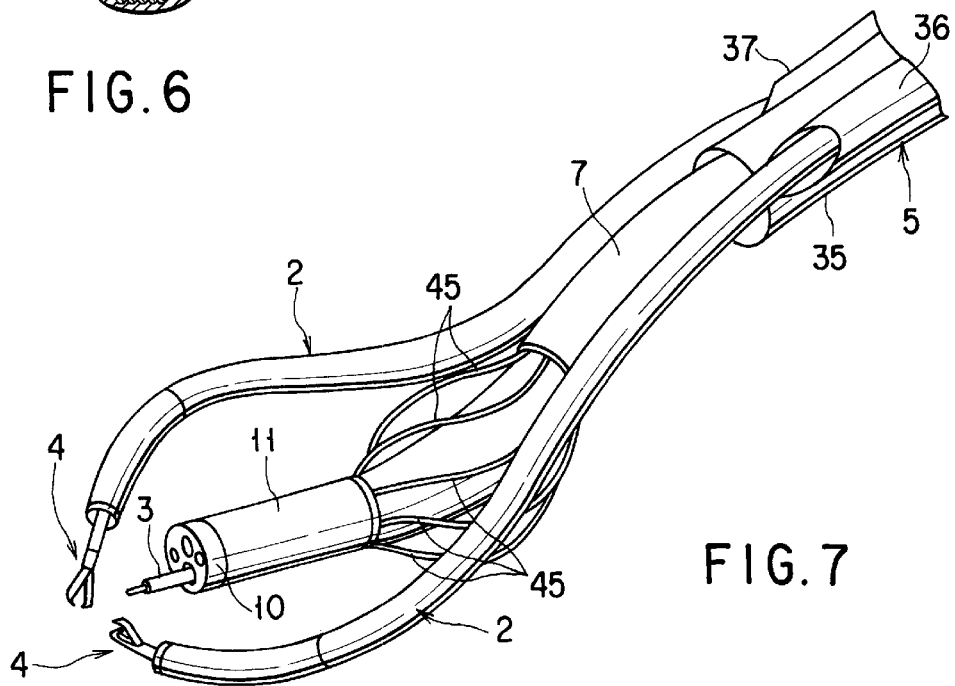
FIG. 7 is a perspective view showing a distal end side section showing a variant of the endoscopic surgery apparatus.

Although, in the present embodiment, as the position adjusting means, the balloon is used by way of example, the present invention is not restricted thereto. As shown in FIG. 7, for example, many wires 45 may be arranged at the outer surface portion of the insertion section of the endoscope 1 such that they provide a basket-like structure capable of being expanded or contracted. In this case, the respective wires 45 are arranged as a diagonal array, such as a helical array, not as an array running along the longitudinal direction of the insertion section 7. This specific diagonal wire array proves convenient because it provides an added area with which the insertion section 21, etc., of the treating tool leading insertion tool 2 is borne/supported by the wires 45.

Further it is considered that, as an operation means for expanding or drawing back the many wires 45, the distal ends of the respective wires 45 are fixed to the outer surface portion of the insertion section 7 and the proximal end sides of the respective wires 45 are drawn back into the insertion section 7 and projected out of he insertion section 7 and the wires 45 are moved back and forth by the operation at the proximal operation section 8. By the operation at the proximal operation section 8 of the endoscope 1, the respective wires 45 are wholly deformed away from the outer peripheral surface of the insertion section 7 and expanded into a basket-like configuration and the relative distance of the basket-like structure to the insertion sections 7 of the treating tool leading insertion tools 2 is adjusted by the extent of expansion.

Further, as a system for deforming the wires 45 away from the outer peripheral surface of the insertion section 7, not only the wires 45 may have their proximal end side portions pushed ahead toward their distal end side but also the wires may be of such a type that the wires are brought from a state in which they are spirally wound on the insertion section 7 to a state in which they are loosely wound back into an expanded configuration.

Here, the first treating tool 3 passed through the channel of the endoscope 1 is comprised of a surgical knife 46 capable of resecting the living tissue of a patient and blocking bleeding through coagulation with the use of a high-frequency current and the second treating tools 4 passed through the channels of the respective treating tool leading insertion tools 2 are each comprised of grasping forceps 47 for grasping the living tissue.

An explanation will be given below about how to use the endoscopic surgery apparatus of the present embodiment. First, the first tube 35 in the outer tube unit 5 is inserted into the insertion section 7 of the endoscope 1 and displaced toward the proximal end side of the insertion section 7. In this state, the insertion section 7 of the endoscope 1 is inserted into the body cavity of the patient as in the case where an ordinary endoscope is handled for checking. The insertion section 7 of the endoscope 1 is inserted into a body cavity of the patient and, with the insertion section 7 of the endoscope 1 as a guide, a whole of the outer tube unit 5 previously displaced to a retracted position is inserted into the body cavity of the patient.

Since, at this time, the distal ends of the second and third tubes 36 are so formed as to, unlike the first tube 35 inserted into the insertion section 7 of the endoscope 1, have end faces 38 diagonally inclined at the acute angle with respect to the axial directions of the second and third tubes 36 and 37, it is possible to reduce any adverse effect by a friction upon the mucous membrane, etc., of the patient at a time of insertion. It is, therefore, possible to insert the whole of the outer tube unit 5 with a minimal damage to the living tissue.

Figure 12:
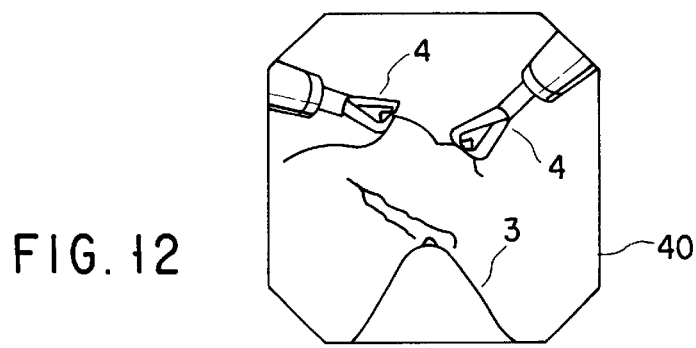
FIG. 12 is an explanatory view for explaining an endoscopic observation image showing a situation in which treating operation is performed on a region of interest in a body cavity of a patient with the use of the endoscopic surgery apparatus.

Then the insertion sections 21 of the treating tool leading insertion sections 2 are inserted into the second and third tubes 36 and 37 of the outer tube unit 5. Under the observation of the endoscope 1, the distal end portions of the insertion sections 21 of the treating tool leading insertion tools 7, together with the insertion section 7 of the endoscope 1, are led to a lesion in the body cavity of the patient. As shown in FIG. 3, the proximal operation section 8 of the endoscope 1 and proximal operation sections 22 of the treating tool leading insertion tools 2 are set on the operation mount 33 and the insertion sections 27 of the treating tools 3 and 4 are inserted into the endoscope 1 and processing tool leading insertion tools 2. In this state, the operator performs a treatment in the body cavity of the patient while observing an endoscopic image 40 as shown in FIG. 12.

Figure 8:
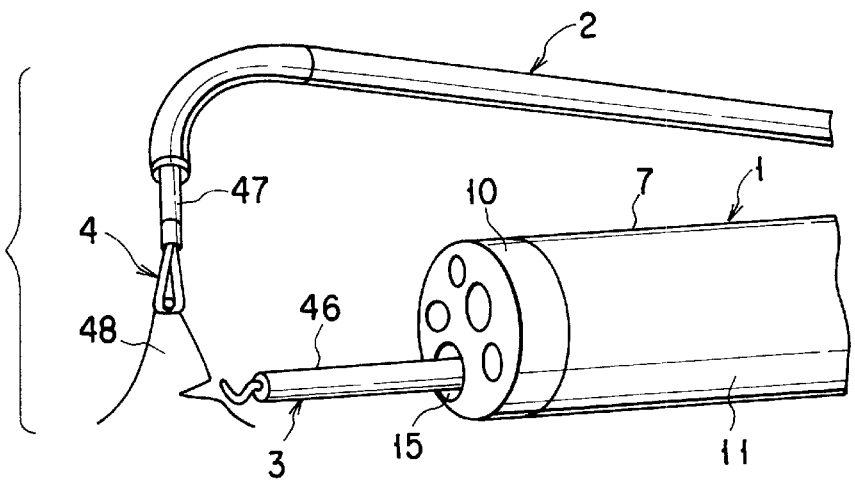
FIG. 8 is a perspective view showing a procedure for performing treating operation on a region of interest in a body cavity with the use of the endoscopic surgery apparatus.

In the case where treatment is performed in the body cavity of the patient, the insertion section 21 of the treating tool leading insertion section 2 is projected, substantially parallel to the insertion section 7 of the endoscope 1, from the distal end of the second tube 36 or third tube 37 as shown in FIG. 8 and the insertion section 21 of the grasping forceps 47 is projected from the distal end of the treating tool leading insertion tool 2. And a living tissue 48 is grasped by the grasping forceps 47 and raised upwardly. The upwardly raised living tissue is cut off from its base portion with the use of a high-frequency surgical knife 46, that is, a surgical knife having a hook at its distal end, which is inserted through the channel of the endoscope 1. In the case where the living tissue 48 including the lesion is cut off by the hook type high frequency surgical knife 46, cutting is made at two places at and around the lesion.

At this time, though not shown in FIG. 8, the balloon 20 attached to the insertion section 7 of the endoscope 1 is inflated as shown in FIG. 1 and, by doing so, the insertion section 21 of the treating tool leading insertion section 21 is properly moved by the balloon to a position away from the insertion section 7 of the endoscope 1 and a relative position is secured between both, so that an operation for grasping the lesion of the living tissue 48 by the grasping forceps 47 is done in a proper direction. That is, a relative distance of the grasping forceps 47 to the insertion section 7 of the endoscope 1 is adjusted in a direction substantially perpendicular to the axial direction of the insertion section 7.

Figure 9:
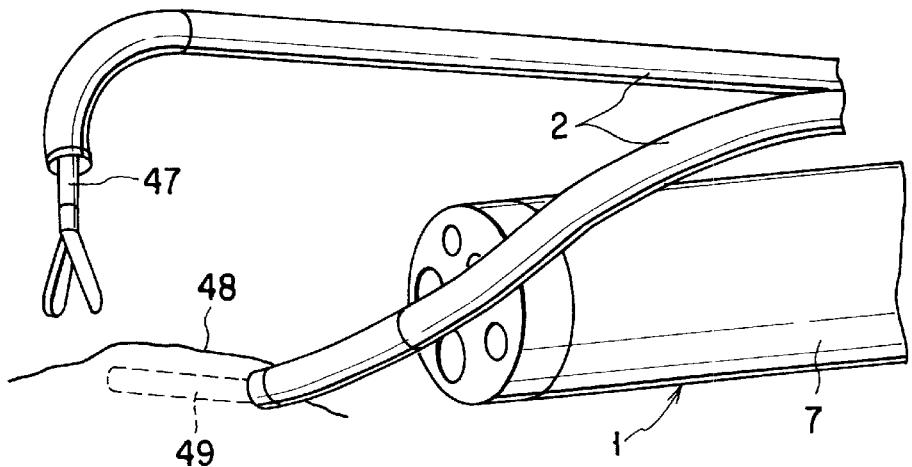
FIG. 9 is a perspective view showing a procedure for performing treating operation on a region of interest in a body cavity with the use of the endoscopic surgery apparatus.
Figure 10:
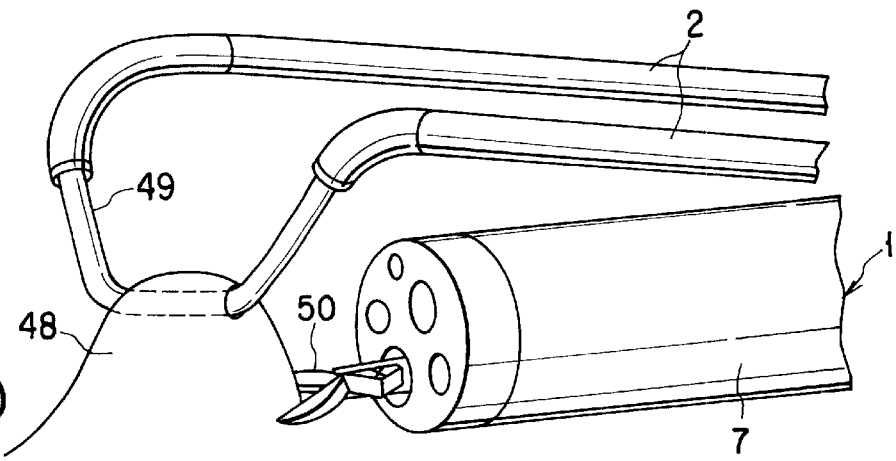
FIG. 10 is a perspective view showing a procedure for performing treating operation on a region of interest in a body cavity with the use of the endoscopic surgery apparatus.

As shown in FIG. 9, after the living tissue 48 has been cut at two places by the high frequency surgical knife 46, a guide wire (treating tool) 49 inserted into one of the two treating tool leading guide tools is pierced into one of the two cut portions and, past an outside wall portion of the organ in the body cavity, brought back into the body cavity from the other cut portion and picked up by the grasping forceps 47 inserted into the other treating tool leading insertion section 2 and pulled back into the treating tool leading insertion tool 2.

By doing so, a whole layer of a target tissue region can be raised upward by the two treating tool leading insertion tools 2 over a wider range and the upwardly raised tissue portion is cut off by scissors forceps 50 inserted through the channel of the endoscope 1.

Figure 11:
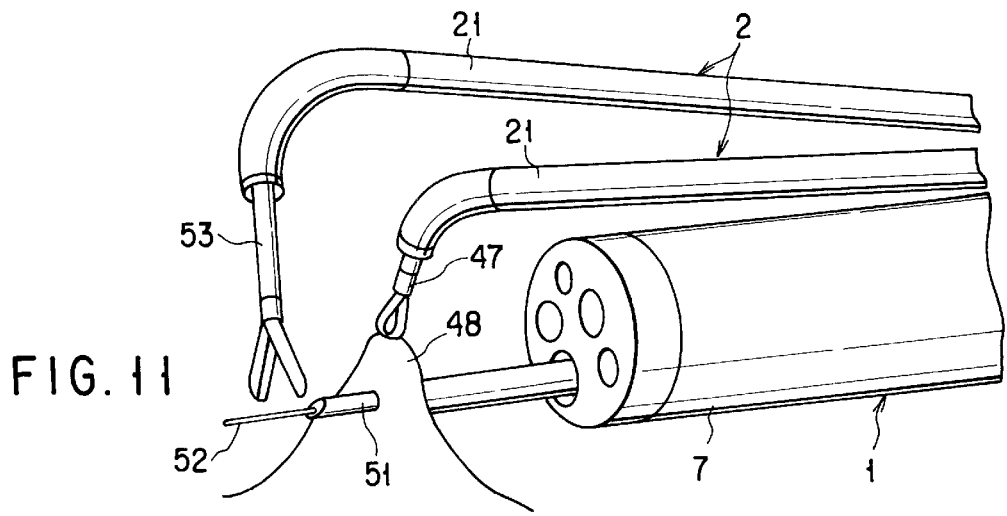
FIG. 11 is a perspective view showing a procedure for performing treating operation on a region of interest in a body cavity with the use of the endoscopic surgery apparatus.

After the living tissue 48 has been cut off, the cut-opened portions are sewed together by using, as shown in FIG. 11, a suture needle (treating tool) 51 passed through the channel of the endoscope 1, sewing thread 52 inserted into the suture needle 51, grasping forceps 47 for grasping the tissue, treating tool leading insertion tool 2 for inserting the grasping forceps 47, thread takeup forceps 53 for taking up the sewing thread 52 and treating tool leading insertion tool 2 for allowing the insertion of the thread takeup forceps 53. The real situation at this time can be observed by an endoscopically observed image as shown in FIG. 12.

Any above-mentioned operations can be done by adjusting the extent of expansion or shrinkage of the balloon 20 attached to the insertion section 7 of the endoscope 1, whereby it is possible to properly control the relative distance between the insertion section 7 of the endoscope 1 and the insertion section 21 of the treating tool leading insertion tool 2 or the insertion section of the treating tool and, for example, it is possible to properly grasp the living tissue by the grasping forceps 47 and properly pull back the tissue opening region.

As explained above, according to the structure and the method of use and function of the present embodiment it is possible to performs treatment in the body cavity under the endoscope 1, such as to make treatment on a diseased region properly, and to do so readily and positively.

Although the present embodiment has been explained in connection with the case of grasping the living tissue in the body cavity of the patient with the use of the treating tool leading insertion tool 2 and grasping forceps inserted through the insertion tool 2, upwardly raising the living tissue and cutting off the region of interest by the hook-type high frequency surgical knife 46 projected from the channel of the endoscope 1, the case of raising the tissue by the guide wire 49 inserted into the treating tool leading insertion tool 2 over a broader range and cutting off the tissue portion by the scissors forceps, and the case of sewing the cut-opening portions together with the use of the grasping forceps 47 and take-up needle 53 inserted into the treating tool insertion tools 2 as well as the suture needle 51 projected from the channel of the endoscope 1 and sewing thread inserted into the suture needle 51, the present invention is not restricted thereto as will be set out in more detail below in connection with various treatments made in the body cavity by the endoscope 1 and treating tool leading insertion tools 2 as well as in connection with practical forms of application.

(Second Embodiment)

Figure 13:
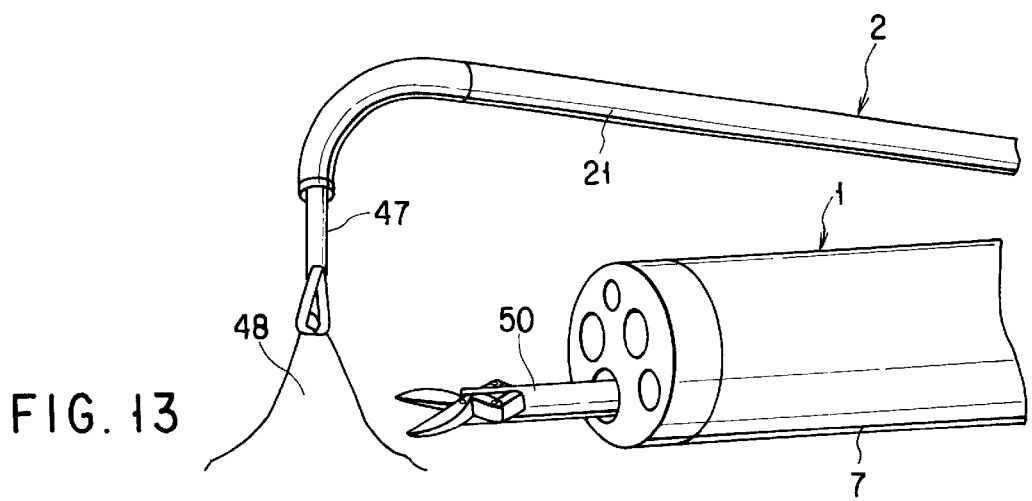
FIG. 13 is a perspective view showing a situation in which treating operation is performed on a region of interest in a body cavity of a patient with the use of an endoscopic surgery apparatus according to a second embodiment.

In the embodiment shown in FIG. 13, a target living tissue portion 48 to be cut off is grasped upwardly by grasping forceps (treating tool) inserted through a treating tool leading insertion section 2 and the upwardly raised living tissue 48 is cut off by scissors forceps (treating tool) 50 inserted through the channel of the endoscope 1. Here, a single treating tool leading insertion tool 2 is used as such and, by leading a distal end portion of the insertion section 7 of the endoscope 1 and treating tool leading insertion tool 2, it is possible to cut off a lesion of a relatively small area along its circumference portion and to more conveniently perform treatment on the lesion of a relatively small area.

(Third Embodiment)

Figure 14:
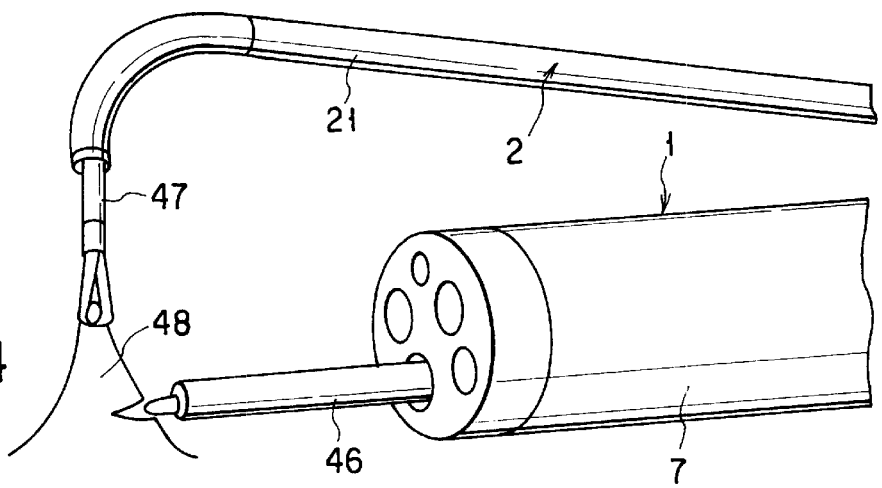
FIG. 14 is a perspective view showing a situation in which treating operation is performed on a region of interest in a body cavity of a patient with the use of an endoscopic surgery apparatus of a third embodiment.

In the third embodiment as shown in FIG. 14, treatment is perform on a lesion of a relatively small area as in the case of the second embodiment. According to the third embodiment, only a diseased mucosa can be locally cut off around its marginal edge portion with the use of a needle-like high frequency surgical knife (treating tool) 46 equipped at its forward end with a high electroconductive metal.

(Fourth Embodiment)

Figure 15:
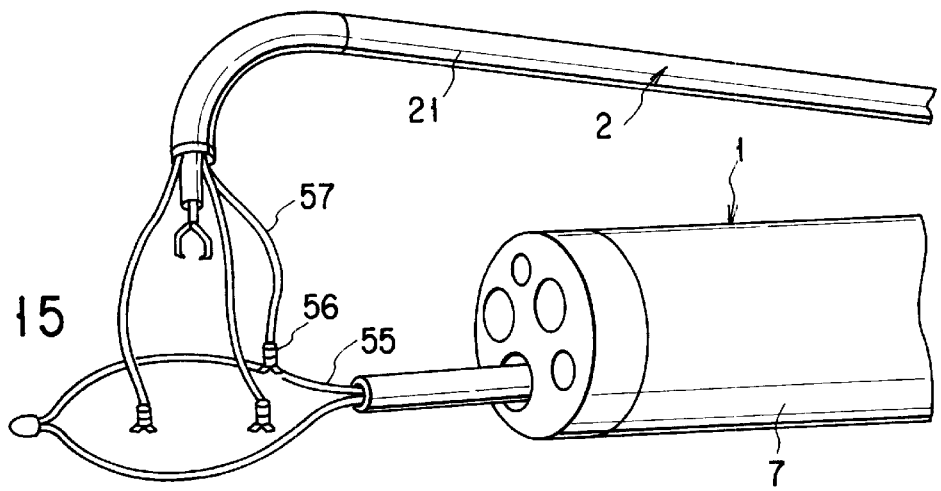
FIG. 15 is a perspective view showing a situation in which treating operation is performed on a region of interest in a body cavity of a patient with the use of an endoscopic surgery apparatus of a fourth embodiment.
Figure 16:
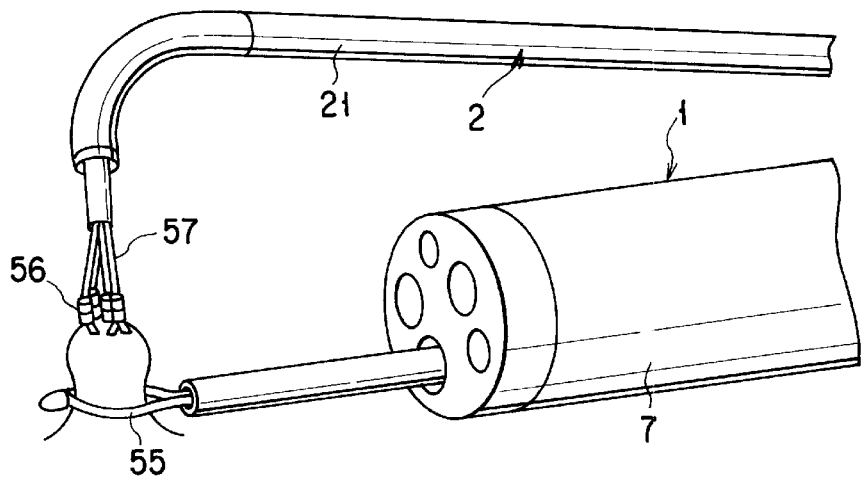
FIG. 16 is a perspective view showing the situation under which treating operation is performed on a region of interest in a body cavity of a patient with the use of the endoscopic surgery apparatus of the fourth embodiment.

A fourth embodiment will be explained below with reference to FIGS. 15 to 16. As shown in FIG. 15, a snare (treating tool) 55 having an opening adequate to surround a diseased region is introduced into the channel of the endoscope 1 and lays a snare with its spread-apart loop placed around the diseased region. A plurality of thread- or wire-equipped clips (treating tools) 56 inserted through the channel of a treating tool leading insertion tool 2 fasten the diseased region around which the loop is set. The threads or wires with clips 56 attached thereto are pull back as shown in FIG. 16 to raise the diseased region upwardly to an adequate extent. By the tightening of the initially laid snare 55 and the supply of a high frequency current it is possible to cut off a whole layer of the diseased region. According to the present embodiment, it is possible to cut off a broader range of the living tissue than by the raising of the grasping forceps 47 as in the previous embodiment, because the diseased region is raised upwardly by many clips 56.

Here, although the diseased region has been explained as being cut off by the snare 55 having a greater loop, it is also effective to upwardly raise the diseased region by the clips 56 and cut off it with the use of the high frequency surgical knife 46 or scissors forceps 50.

(Fifth Embodiment)

Figure 17:
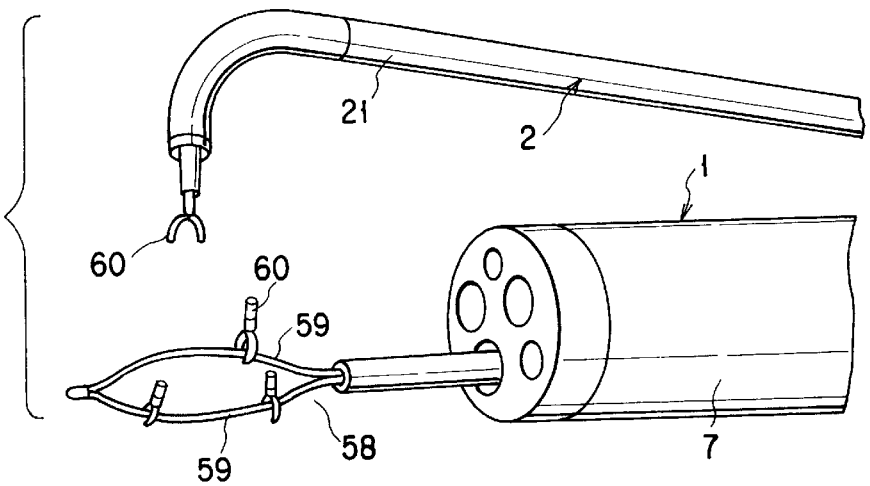
FIG. 17 is a perspective view showing the situation under which treating operation is performed on a region of interest in a body cavity of a patient with the use of an endoscopic surgery apparatus according to a fifth embodiment.
Figure 18:
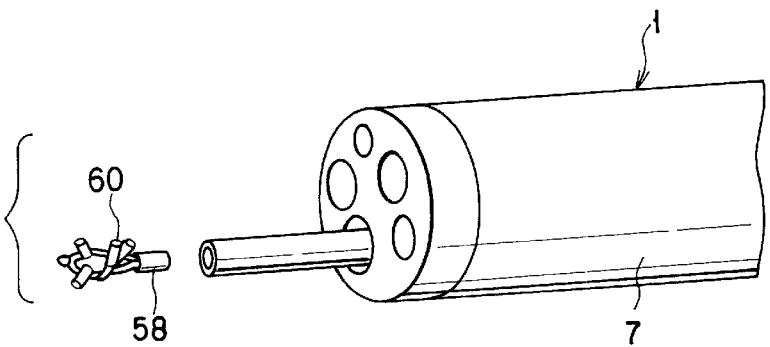
FIG. 18 is a perspective view showing a situation under which treating operation is performed on a region of interest in a body cavity of a patient with the use of the endoscopic surgery apparatus according to the fifth embodiment.

A fifth embodiment will be explained below with reference to FIGS. 17 to 18. This embodiment is applied to the case where, after the cutting off of the living tissue, resultant cut opening portions produced on the inner wall of the body cavity are closely joined into a sealed union. As shown in FIG. 17, a staying snare (treating tool) 58 can be projected out of the channel of the endoscope 1 into the body cavity and, after a diseased portion has been tightly tied together, cut off its forward loop 59. The loop wire 59 of the snare 58 is set at the cut opening area left after the cutting off of the living tissue.

Then the clips (treating tool) 60 are introduced from above the loop wire 59 into the body cavity with the use of a treating tool leading insertion tool 2. The loop wire 59 of the staying snare 58 and tissue at the marginal edge of a living tissue opening are, while being grasped, fastened at a plurality of places by clips 60. Then the loop wire 59 of the snare 58 is tightened while being fastened by the clips 60. At this state, the cut opening portion of the living tissue together with the loop wire 59 of the snare are closed by the tightening of the staying snare 58. After being completely tightened, the loop wire 59 of the staying snare 58 is cut off from the proximal end side and, as shown in FIG. 18, the cut opening portions are closely joined into a sealed union.

Although not shown in detail, it may be considered that the sealingly joined portions of the cut opening tissue are fastened by another clip, by coating a bonding agent there and so on.

(Sixth Embodiment)

Figure 19:
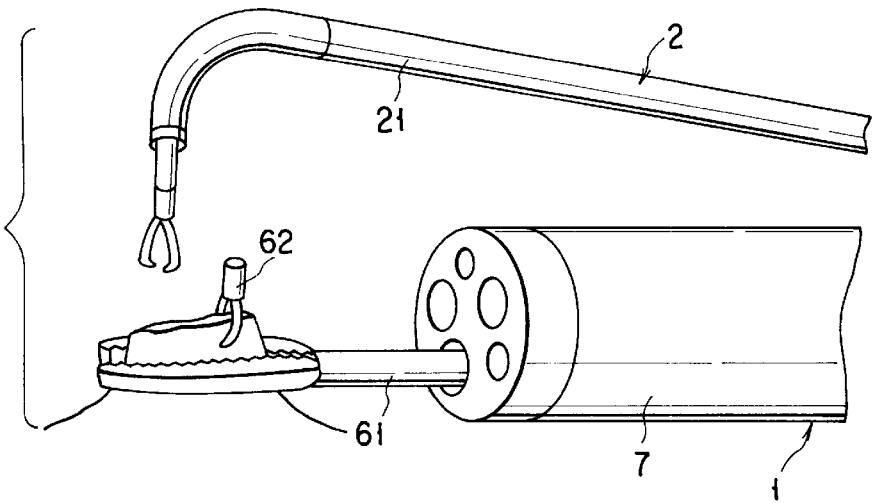
FIG. 19 is a perspective view showing a situation under which treating operation is performed on a region of interest in a body cavity of a patient with the use of an endoscopic surgery apparatus according to a sixth embodiment.

The sixth embodiment of the present embodiment will be explained below with reference to FIG. 19. In this embodiment, cut opening tissue portions are grasped by lengthy grasping forceps (treating tools) 61 inserted through the channel of the endoscope 1 and joined together and, as shown in FIG. 19, the joined area is fastened by a clip 62 with the use of a treating tool leading insertion tool 2.

Figure 20:
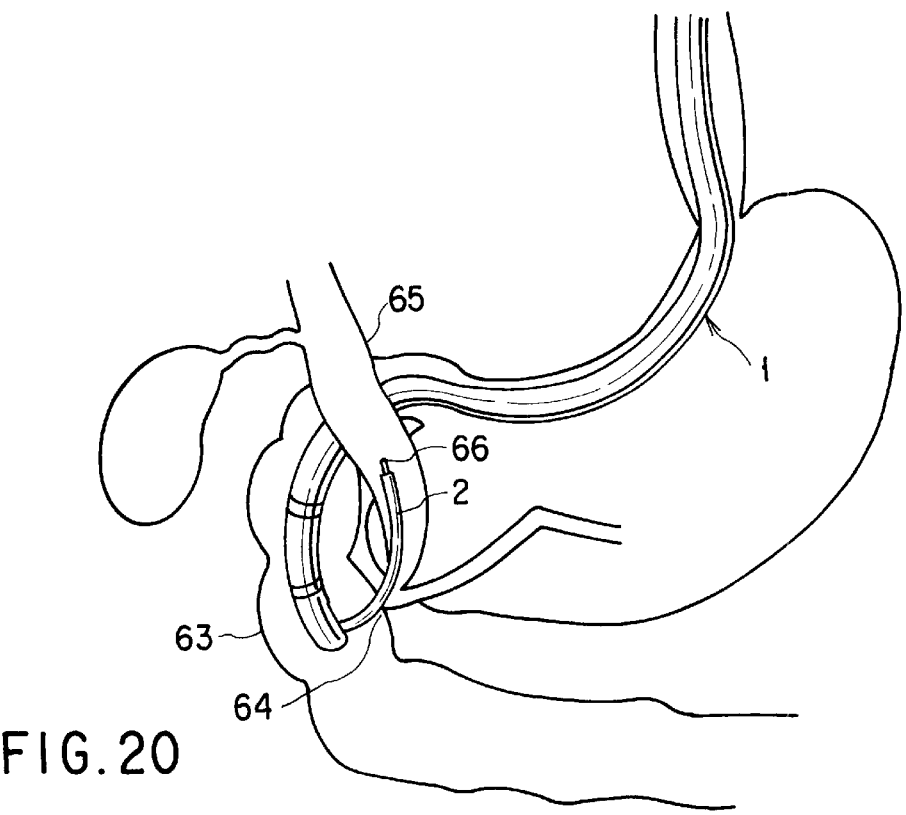
FIG. 20 is an explanatory view showing another applied form of above-mentioned endoscopic surgery apparatus.
Figure 21:
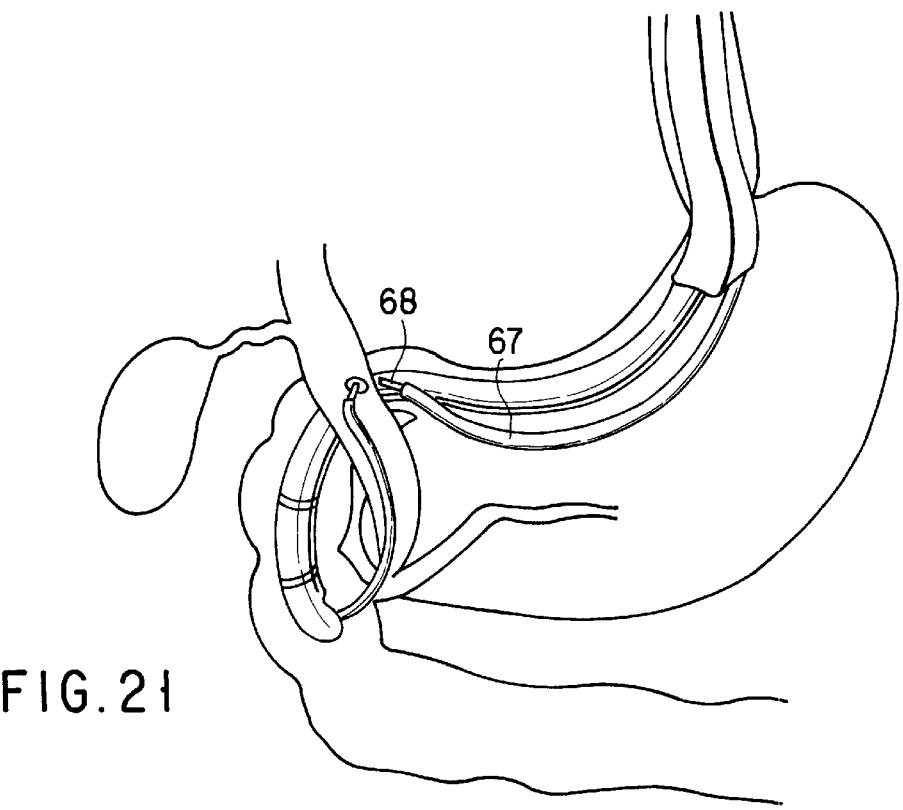
FIG. 21 is an explanatory view showing another applied form of above-mentioned endoscopic surgery apparatus.

Although, in the above-mentioned embodiments, a plurality of insertion tools are inserted into the body cavity and the technique of resecting, cutting off, the sealing union, sewing, etc., in the body cavity is applied to the upper digestive system, such as the esophagus, stomach, duodenum, etc., the technique can be expected to be applied to the lower digestive system, that is, the large intestine, in terms of its function or effect. In addition, as an application of the outer tube unit it is also possible to make a bypass therapy by creating a bypass, as shown in FIGS. 20 and 21, between a treating tool 66 operated by a treating tool leading insertion toll 2 inserted past the duodenal papillae into the biliary duct 65 and the endoscope 67 additionally inserted down to the duodenum 63 or a treating tool 68 inserted through the channel of the endoscope.

(Seventh Embodiment)

The seventh embodiment of the present invention will be explained below with reference FIGS. 22 to 27.

FIG. 22 is a perspective view diagrammatically showing the situation under which the seventh embodiment is used. In the seventh embodiment, a flexible insertion section 102 of a two-channel endoscope 101 is orally inserted into the body cavity of a patient 103 so that the operation procedure, such as the resection of a diseased region, is performed in the body cavity. The doctor inserts the insertion section 102 of the endoscope 101 down to a target diseased region and a proximal operation section 105 of the endoscope 101 is securely set in place on an endoscope holder 104. The cutting off, etc., of the diseased region of the patient is performed on the proximal end side by operating treating tools inserted through the channel of the endoscope 101, for example, a grasping forceps (treating tool) 106 and electrical surgical knife (treating tool) 107. The surgical knife 107 is connected to an electrical knife drive unit, not shown. By operating a foot switch, not shown, by an ON/OFF fashion a high frequency wave is supplied to the surgical knife, thus causing the living tissue to be cut off and coagulated.

The insertion section 102 of the endoscope 101 comprises a distal end section 110, bending section 111 adjacent the distal end section and a flexible tube 112 connected to the distal end side of the bending section 111. The distal end section 110 has a distal end block (body member) 108 as shown in FIG. 23. The distal end block 108 is covered with a distal end cover 109 made of a resin, such as polysulfone. As shown in FIGS. 23 and 24, the distal end section 110 includes an image guide lens in an observation optical system having various lenses and CCD, a light guide lens 114 in an illumination optical system, distal end nozzle unit 115 opened toward the observation window 113 to wash any surface smudge by supplying air and water, a sub-water-channel outlet 116 supplying clean water, etc., into the body cavity, and distal end openings 123, 124 of the channels 121, 122. The respective distal end openings 123, 124 are arranged one to the left and one to the right below the observation window 113 as shown in FIG. 23. The distal end openings 123, 124 of the channels 121, 122 are provided correspondingly to lower area portions in an endoscope field observed in a usual state.

On the other hand, a light guide cable 135 is connected to the proximal operation section 105 of the endoscope 101.

An angle knob 136 is provided at the proximal operation section 105 and operated when the bending section 111 is to be bent. A two processing tool insertion inlet section 137 is provided at the proximal operation section 105 to lead to the two channels 121, 122. Various kinds of operation buttons, not shown, for enabling a switching among the air supply, water supply, suction, etc., a operation box 139 for various switches, etc., are provided at the proximal end section 105.

The first channel 121 and second channel 122 are individually separated in the insertion section 102 as shown in FIG. 23 and arranged in a parallel array along the longitudinal center axis of the insertion section 102. The distal end opening 123 of the first channel 121 is formed in a straight way along the longitudinal center axis and has an equal diameter. The distal end opening 124 of the second channel 122 provides an inclined surface 125 situated on a side opposite to that of the first channel 121 and inclined, at the distal end side, away from the first channel 121.

A position adjusting device is provided at the distal end opening 124 of the second channel 122 for adjusting a relative distance, in a direction substantially perpendicular to the axial direction of the insertion section 102 of the endoscope 101, between the insertion section of the treating tool inserted through the first channel 121 and the insertion section of the treating tool inserted through the second channel 122. In more detail, the device is so constructed as will be set out below. A forceps raising base receiving recess 126 is provided in an inner surface portion situated in the first channel 121 side. A forceps raising base 127 is received in the forceps raising base receiving recess 126. The forceps raising base 127 has its proximal end side pivotally attached and fixed to the distal end block 108 and the forceps raising base 127 is swingable about a pivotal pin 128 so that the distal end side portion can be freely brought to a raised position and a lying-down position. A forward end of a forceps raising wire 129 is coupled to a side wall portion of a distal end portion of the forceps raising base 127. By pulling back the forceps raising wire 129 toward the proximal end side, the forceps raising base 127 is raised to allow the distal end side portion of the treating tool which is projected form the distal end opening 124 to be moved from the lying-down position parallel to the first channel 121 toward a direction away from the first channel 121. This raising mechanism has a function of bending the distal end portion of the treating tool which is introduced through the second channel 122 toward the direction away from the distal end section of the treating tool introduced through the first channel 121.

The forceps raising wire 129 is guided toward the proximal end section 105 past a guide tube 130 placed in the insertion section 102 and coupled to a traction mechanism operated by a raising lever 131 on the proximal end section 105.

The operation of the embodiment will be explained below. The insertion section 102 of the endoscope 101 is introduced into the body cavity and the proximal operation section 105 of the endoscope 101 is fixed to the endoscope holder 104. The treating tools used are inserted from the treating tool insertion sections 137 of the proximal end section 105 into the channels 121, 122 and the distal end portions of the treating tools are projected from the distal end portions 123, 124 into the body cavity. For example, the electrical surgical knife 107 is inserted into the first channel 121 and the grasping forceps 106 is inserted into the second channel 122. The grasping forceps 106 and electrical surgical knife 107 are guided in parallel along a longitudinal center direction of the insertion section 102 of the endoscope 101. Usually, the distal end portions of these are projected forwardly in parallel along the longitudinal center axis of the insertion section 102.

Figure 25:
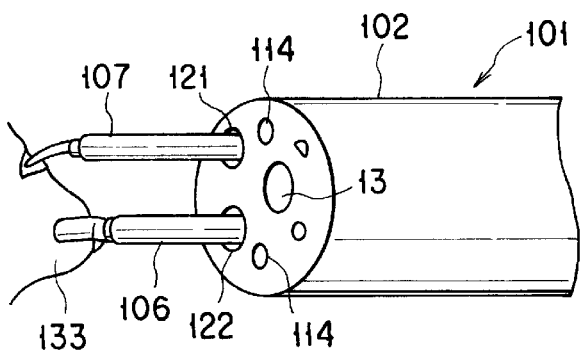
FIG. 25 is an explanatory view showing a situation under which an endoscope according to the seventh embodiment is used.
Figure 27:
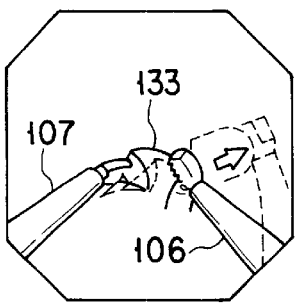
FIG. 27 shows a visual-field image of the endoscope in use.

FIG. 25 shows the case where, grasping a diseased portion 133 by the grasping forceps 106, a surrounding tissue portion including the diseased portion is resected by an electronic surgical knife 107. FIG. 27 shows an image in a visual field when this procedure is performed with the use of the endoscope 101. When the living tissue portion is cut opened by the electric surgical knife 107, the surgical knife can be easily and accurately pushed against the living tissue including the diseased portion because the diseased portion is grasped/held by the grasping forceps 106. In this pushed state, a cut-opening/tissue coagulation-performing high frequency current is applied by the electrical surgical knife 107 to the diseased portion to resect the living tissue.

Figure 26:
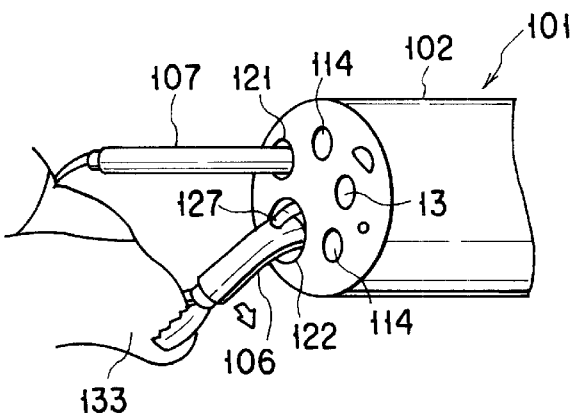
FIG. 26 is an explanatory view showing a situation in which the endoscope according to the seventh embodiment is used.

With the cut-opening of the tissue advanced to some extent, the cutting cross-section becomes harder to observe in which case the forceps raising base 127 is raised to move the forward end portion of the grasping forceps 106 toward a direction of an arrow in FIGS. 26 and 27. And the diseased portion 133 is pulled to the right in FIG. 27 and the cutting cross-section of the diseased portion is wide-opened at which time the electric surgical knife 107 is again pushed against the cutting cross-section. By continuing the cut operation on the living tissue including the diseased portion 133 it is possible to efficiently cut off the diseased portion at one continuous operation.

Normally, the living tissue is pliable and, if a hard bar-like means, such as the electric surgical knife 107, is to be pushed against and cut off the living tissue, then the tissue portion is pliably displaced away from the surgical knife. For this reason, with the diseased portion pulled by the grasping forceps 106 while being under a tension, the electric surgical knife 107 can be positively pushed against the diseased portion to ensure the easiness with which the diseased portion is cut off.

As set out above, in the case where a pliable living tissue is to be cut off, this operation can be more easily done while fixing the diseased portion 133 than otherwise and it is done without involving the displacement of the living tissue. In the present embodiment, since the grasping forceps 106 is inserted into one of a plurality of channels and, while grasping and fixing the diseased portion 133 by the forceps 106, the cutting off of the diseased portion 133 is performed by the electric surgical knife 107 inserted through another channel, thus ensuring the easiness with which the cutting-off operation is performed. Further, the direction in which the grasping forceps 106 is raised by the forceps raising base 127 of the raising mechanism is away from the electrical surgical knife 107 of the associated treating tool, that is, the forward sections of both the treating tools are relatively moved in a direction away from each other. It is, therefore, possible to perform the above-mentioned operation positively while cut-opening the living tissue including the diseased portion 133. As a result, the living tissue can be more deeply cut-opened than by the conventional method. Further, the cut-opening operation of the diseased portion 133 is performed in a continuous separation way and done so while applying some tension to the cut-opening tissue. It is possible to readily and efficiently perform the cut-opening operation.

Although, in the seventh embodiment, the electrical surgical knife is selected as a means of cutting off the diseased portion, it is also possible to use a treating tool, such as scissor forceps, for mechanically cutting off a living tissue as well as a treating tool using a laser and ultrasonic wave.
(Eighth Embodiment).

The eighth embodiment of the present invention will be explained below with reference to the accompanying drawings.

An endoscope 101 of the present embodiment has three channels, that is, a first channel 141, second channel 142 and third channel 143 with the second channel 142 provided between the first channel 141 and the third channel 143. The distal end openings of the first channel 141 and third channel 143 each have a forceps raising mechanism having a forceps raising base for moving a treating tool inserted through the corresponding insertion section in a direction away from the second channel 142 as in the case of the previous embodiment. The respective forceps raising mechanism raises the insertion section of the treating tool by bending the insertion section of the treating tool outwardly in a direction substantially perpendicular to the axial direction of an insertion section 102 of the endoscope 101. That is, this provides a mechanism for adjusting a relative distance between the insertion sections of the paired treating tools in a direction substantially perpendicular to the axial direction of the insertion section of the endoscope.

The forceps raising bases provided at the first channel 141 and the third channel 143 are independently operable by forceps raising levers provided on a proximal operation section as in the case of, for example, the seventh embodiment. The other arrangement of this embodiment is the same as that of the seventh embodiment.

Figure 28:
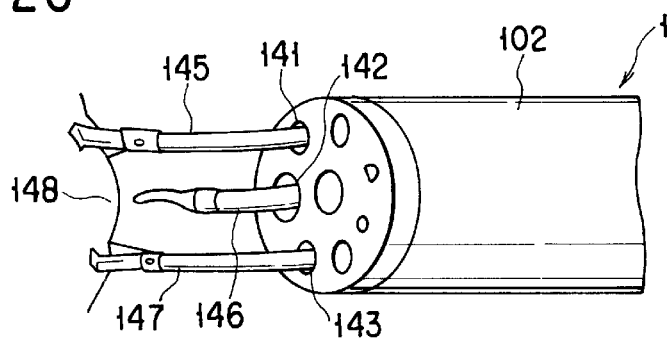
FIG. 28 is an explanatory view showing a situation under which an endoscope according to an eighth embodiment is used.
Figure 29:
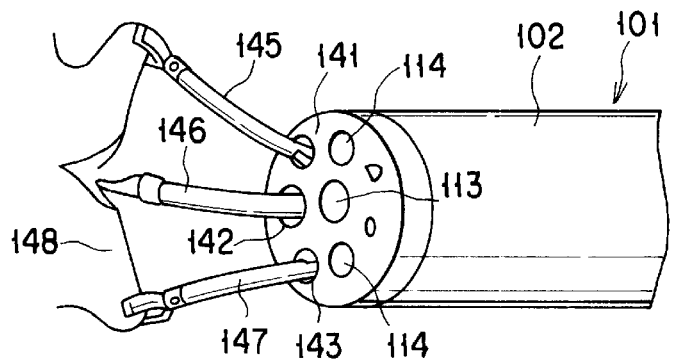
FIG. 29 is an explanatory view showing a situation under which the endoscope according to the eighth embodiment is used.
Figure 30:
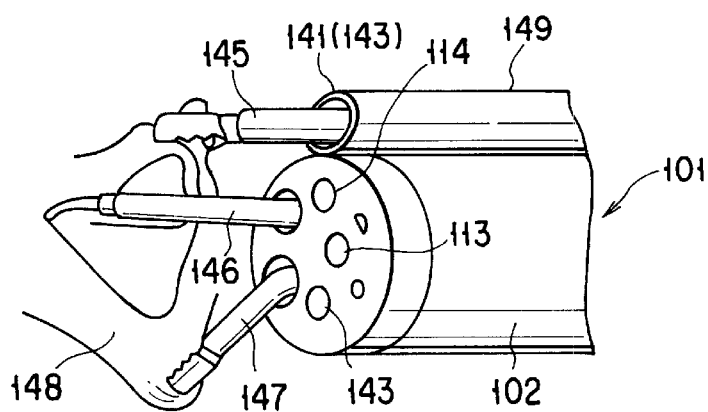
FIG. 30 is an explanatory view showing a variant of an endoscope, in use, according to a ninth embodiment.

Now the operation of this embodiment will be explained below. As shown in FIG. 28, with the endoscope introduced into the body cavity of the patient, first grasping forceps 145 is inserted into the first channel 141 of the insertion section 102 of the endoscope 101, an electric surgical knife 146 is inserted into the second channel 142 of the endoscope 142 and second grasping forceps 147 is inserted through the third channel 143 of the endoscope. And the portion of a living tissue 148 is grasped by the first grasping forceps 145 and second grasping forceps 147. In this state, an electrical surgical knife 146 is projected in an area between the first grasping forceps 145 and the second grasping forceps 147. The living tissue 148 is cut opened by a high frequency current while pushing the forward end of the electric surgical knife 146 against the living tissue 148 of interest. Then, the forceps raising bases are raised by the first channel 141 and third channel 143 and the forward ends of the first grasping forceps 145 and second grasping forceps 147 are moved away from each other. At this time, the respective forceps raising mechanisms are independently operated and, by doing so, the forward end of the electric surgical knife 146 is so adjusted as to be abutted against the cut opening portion of the living tissue 148. Subsequently, the electric surgical knife 146 is again projected to continue the cut opening of the living tissue 148.

According to this embodiment, a surgical operation, such as a cut opening, is done while grasping the living tissue 148 of interest by the two grasping forceps 145, 147. It is possible to more readily and positively cut open the living tissue 148 of interest than by fixing the living tissue 148 by the single grasping forceps as in the case of the seventh embodiment. By individually and independently adjusting raised states of the respective grasping forceps 145, 147 a target cut opening portion of the living tissue 148 can be readily moved closer to the forward end of the electric surgical knife 146.

Although, in the above-mentioned embodiment, the respective forceps raising mechanisms are mutually independently moved, the two forceps raising mechanisms may be moved by one forceps raising lever in interlock with each other. Since it is not necessary to operate a plurality of forceps raising levers, it is easier to operate by one operator.

A detachable external channel tube (tube member) 149 may be formed on an insertion section 102 of an endoscope 101 in a structure of the seventh embodiment shown in FIG. 7 and, by doing so, it is possible to provide a first channel 141 or a third channel 143. In this case, a means by which the channel tube 149 is mounted along the insertion section 102 of the endoscope 101 may be detachably mounted on the insertion section 102 of the endoscope.

The present invention can be applied to the surgery systems as will be set out below.

(Section 1 of Another Endoscopic Diagnostic System)

An endoscopic system for this treatment is equipped with an ordinary endoscope 151 and the tube-like treating tool insertion tool 152 as shown in FIGS. 31 to 36. The treating tool insertion tool 152 is neither equipped with an optical system, such as an image guide/light guide, fitted with a normal endoscope nor equipped with an air/water supply tube system. The insertion tool 152 is simply equipped with a channel 154 through which the treating tool is inserted and, except this aspect, it has the same structure as that of the ordinary endoscope. Further, the insertion section 153 of the treating tool insertion tool 153 has a distal end section 156 opened at the forward end opening of a channel 154 and a bending section 157 which is bent by the operation of the proximal operation section, not shown.

A single channel 159 is provided at an insertion section 158 of the ordinary endoscope 151 and, through the channel 159, a staying snare 161 is inserted into a body cavity of a patient. The snare 161 has a sheath 162 and snare wire 163 and the snare wire 163 is detached from the distal end of the sheath 162.

And the insertion section 158 of the endoscope 151 and insertion section 153 of the treating tool insertion tool 152 are inserted into the body cavity of the patient. At this time the forceps insertion tool 152 is inserted along the insertion section 158 of the endoscope 151 into the body cavity of the patient. Thereafter, the staying snare 161 is introduced through the channel 159 of the endoscope 151 into the body cavity of the patient and, through the channel 154 of the processing tool insertion tool 152, a clip device or grasping forceps 164 is introduced into the body cavity of the patient.

Figure 31:
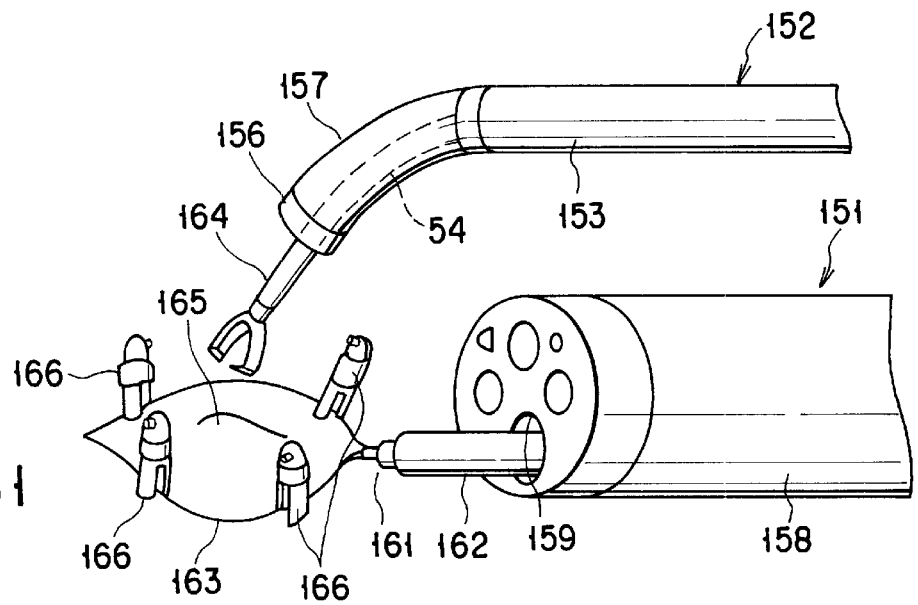
FIG. 31 is an explanatory view showing another treating endoscope in use.

And shown in FIG. 31 the snare wire 163 of the staying snare 161 is placed around a diseased portion 165. The thus placed snare wire 163, together with a living tissue portion including the diseased portion 165, is grasped with a plurality of clips 166 supplied by the clip device or grasping forceps 164. That is, the respective clips 166 fastens the snare wire 163 and living tissue portion together and keep them steady.

Figure 32:
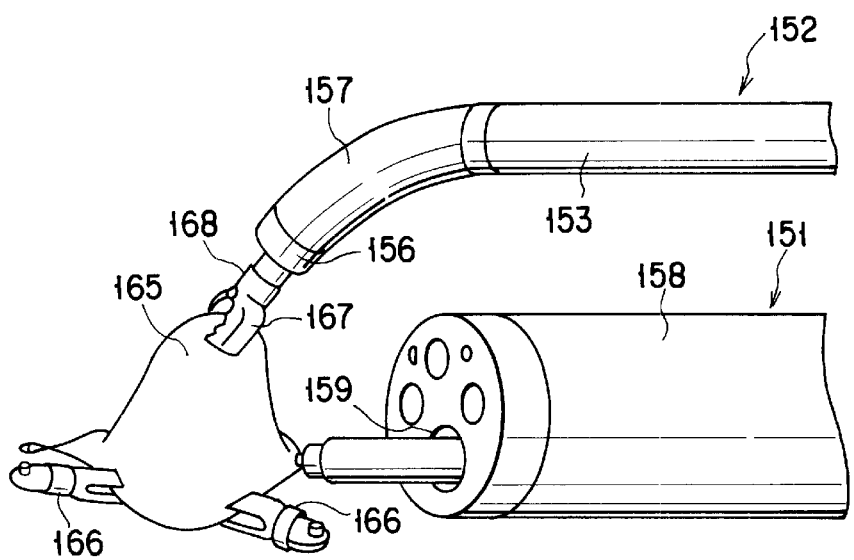
FIG. 32 is an explanatory view showing the above-mentioned treating endoscope in use.
Figure 33:
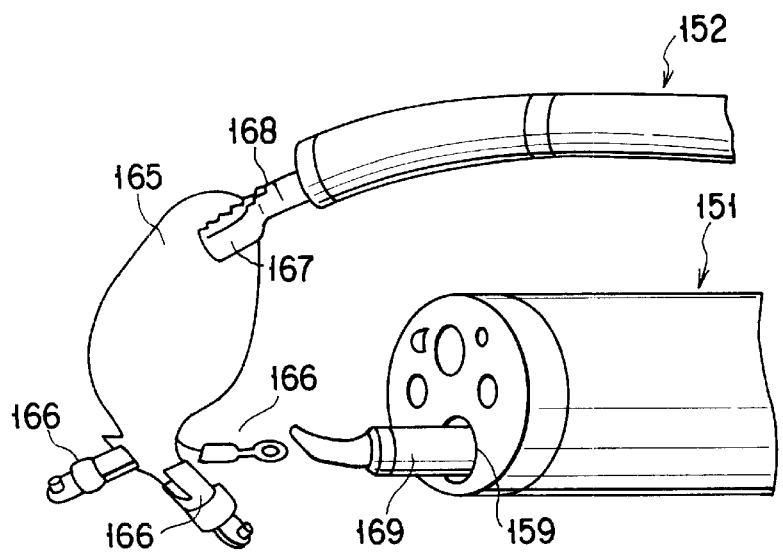
FIG. 33 is an explanatory view showing the above-mentioned treating endoscope in use.
Figure 34:
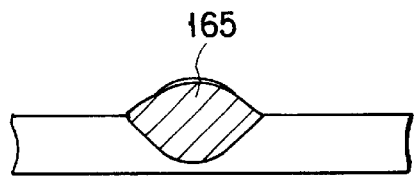
FIG. 34 is an explanatory view showing a situation in which the living tissue portion is treated by the treating endoscope.
Figure 35:
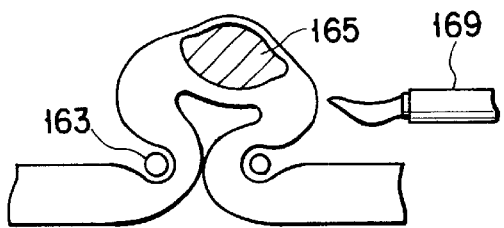
FIG. 35 is an explanatory view showing a situation in which the living tissue portion is treated by the treating endoscope.
Figure 36:
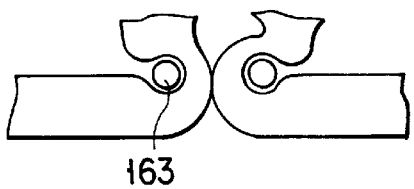
FIG. 36 is an explanatory view showing a situation in which the living tissue portion is treated by the treating endoscope.

As shown in FIG. 32, a grasping forceps 168 having a greater forward end grasping section 167 is inserted through the channel 154 of the forceps insertion tool 152 and, when the diseased portion 165 is grasped by the grasping forceps 168 and the bending of the bending section 157 of the forceps insertion tool 152 is regained back to its original form and somewhat pulled back toward the operator. Then, as shown in FIG. 32, the diseased portion 165 including its own muscle layer is grasped and raised. That is, as shown in FIG. 34, the diseased portion which is an originally flattened region is raised. The raised portion is bound tight by the pulling back of the snare wire 163 of the staying snare 161 and, as shown in FIG. 35, a whole region including a neighboring muscle layer can be tightly bound by the snare wire 163 of the staying snare 161. In this state, an electric surgical knife 169 is inserted through the channel 159 of the endoscope 151 and a surrounding tissue edge portion around the diseased portion 165 is cut opened as shown in FIGS. 33 and 36 and cut off.

According to the present invention, at the cutting of the whole region including its own muscle layer, it is initially bound tight by the staying snare, so that, even after the cutting off of the diseased portion 165, there is no hole left there.

Normally, the abdominal cavity outside the tract organ is in a germ-free state while, on the other hand, some forms of germs are often present inside the tract organ represented by the large intestine. For this reason, if any perforation is produced in the tract organ, the germs are scattered in the germ-free abdominal cavity there is a risk that the patient will suffer from the peritonitis, etc. According to the present invention, there is no risk of the patient suffering from any such diseases.

The forceps insertion tool used in the present method is inserted along the endoscope and at least one portion of the tool may be fixed at the endoscope's insertion section. In this case, the positional relation between the endoscope and the forceps insertion tool is uniquely determined and the forceps inserted through the forceps insertion tool emerges in a given range on an endoscope image, thus ensuring an improved operability. As a fixing method, a heat-shrinkable tube-like member may be used except at the bending section of the endoscope and forceps insertion tool.

(Section 2 of Another Endoscopic Diagnostic System)

This treating type endoscopic system is used to raise a whole area of a diseased portion without depending upon the grasping forceps. This system will be explained below with reference to FIGS. 37 to 40.

Figure 38:
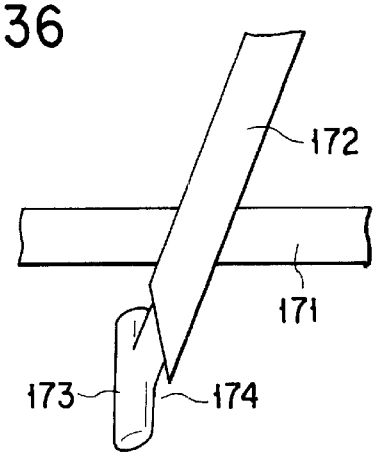
FIG. 38 is an explanative view showing a situation under which treating operation is performed on the living tissue portion by the treating endoscope (FIG. 37)
Figure 37:
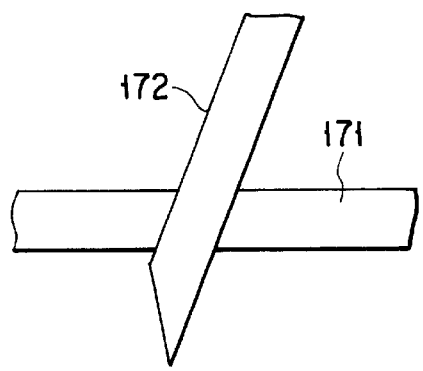
FIG. 37 is an explanatory view showing a situation under which treating operation is performed on a living tissue portion by another treating endoscope.

First, as shown in FIG. 37, a needle 172 like a syringe needle 172 is stabled into a living tissue portion 171 such as a muscle layer near a diseased portion to be raised. As shown in FIG. 38, a raising jig 174 with a T-shaped forward end engaging section 173 inserted through the needle 172 is inserted into a living tissue portion 171. The forward end engaging portion 173 of the raising jig 174 is collapsed into a substantially straight line form, but, upon being projected from the distal end of the needle 172, is spread back to a T shape. Then, as shown in FIG. 38, the needle 172 is pulled back while the raising jig 174 is exposed. As shown in FIG. 40, when the raising jig 174 is pulled back, the forward end engaging portion 173 is caught onto the living tissue portion 171, so that the diseased portion including its own muscle area can be raised. In this state, the diseased portion, etc., is cut opened by an electrical surgical knife 175 for instance and is removed.

(Section 3 of Another Endoscopic Diagnostic System)

FIGS. 41 to 43 show another form of a treating tool insertion tool. Here, a treating tool insertion tool 152 is not equipped with an optical system and air/water supply tube system except a channel 154 as in the case of the above-mentioned forceps insertion tool, but a distal end opening 155 of the channel 154 of the treating tool insertion tool 152 is provided at a side surface of its distal end opening 155. A raising mechanism is provided at the distal end opening 155 of the channel 154 and has a forceps raising base 181 for raising a treating tool inserted into the channel 154.

FIG. 42 shows a state in which an ordinary endoscope 151 and treating tool insertion tool 152 are used in combination.

The treating tool insertion tool 152 bends a bending portion 157 of the insertion section 153 while raising the forceps raising base 181. By doing so, a diseased portion 182 is sandwiched relative to the bending section 157 and grasped by grasping tools 183 at the opposite side of the endoscope 151. And the diseased portion 182 is cut off by an electric surgical knife 184 inserted through a channel 159 of the endoscope 151.

According to the present invention, with the diseased portion 182 sandwiched, the diseased portion 182 is grasped by the grasping forceps 183 from the opposite side of the endoscope 151 and the field of vision of the endoscope 151 is prevented from being blocked.

Further, FIG. 43 is a state in which the diseased portion 182 is cut off from the side opposite to a side on which the endoscope 151 is inserted. First, the diseased portion 182 is grasped by the grasping forceps 183 with the use of the treating tool insertion tool 152, so that the diseased portion 182 is raised. By bending the endoscope 151 in a tube bore toward the diseased portion 182, the diseased portion 182 is cut off by the electric surgical knife 184 from the side opposite to the side on which the endoscope 151 is inserted.

(Section 4 of Another Endoscopic Diagnostic System)

FIGS. 44 to 47 show a case where the reflux esophagitis, such as the Barrett syndrome is treated with the use of a treating endoscope 101 having two channels as in the case of the seventh embodiment.

As shown in FIG. 44, with the insertion section 102 of the endoscope 101 inserted into the stomach in a substantially straight state, greater grasping forceps 186 is inserted into one channel 121 and a greater clipping device 187 is inserted into the other channel 122. The forward end portions of the grasping forceps 186 and clipping device 187 are projected from the distal end of an insertion section 102 of the endoscope 101.

Subsequently, as shown in FIG. 45, a bending section 111 of the insertion section 102 of the endoscope 101 is bent, a distal end section 110 of the insertion section 102 is bent as if looking up the cardia part of the stomach from below and the cardia part of the stomach including the tissue of the stomach is grasped. And as shown in FIG. 46, the tissue portion of both the grasped esophagus and the adjacent stomach part is fastened by the greater clipping device 187 to keep the grasped tissue portion steady. By a repeated operation, an artificial valve is created between the esophagus and the stomach part to prevent the reflux of a gastric juice.

(Section 5 of Another Endoscopic Diagnostic System)

This is a treating type endoscopic system by which a treating procedure is made with the use of a side-viewing type endoscope. This procedure will be explained below with reference to FIGS. 48 to 50.

Figure 48:
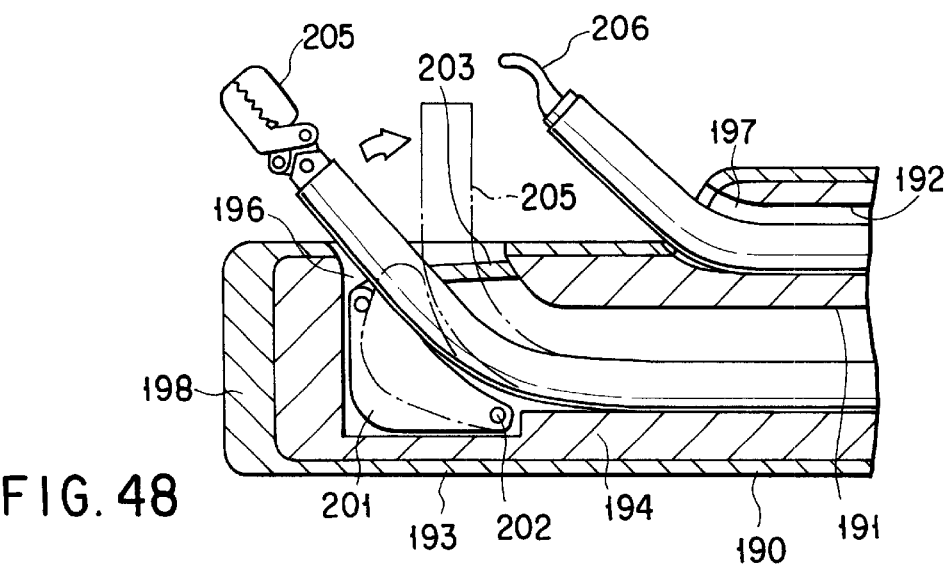
FIG. 48 is a longitudinal cross-sectional view showing a distal end section of further treating endoscope.

FIG. 48 is a longitudinal view showing a distal end portion, and its neighborhood, of an insertion section 190 of a side-viewing type endoscope equipped with two or more channels. As shown in FIG. 48, a first channel 191 and second channel 192 are provided in an insertion section 190 and these channels 191 and 192 are independently provided, extending from their forceps insertion inlets provided at a proximal operation section of the endoscope not shown to a distal end section 193 of an insertion section 190 and communicate with their distal end portions 196 and 197 formed at a distal end block (body member) 194 of the distal end section 193. Further, these channels 191 and 192 are arranged one on an upper side and one on a lower side as viewed on an elevational view along a center axial direction of the insertion section 190 of the endoscope.

The distal end block 194 of the distal end section 193 includes, though being not shown, various kinds of lenses, CCD/light guide cable, air/water supply tube passage, distal-end nozzle unit, and so on. The distal end block 194 is covered with a distal end cover 198 made of a resin, such as polysulphone.

A forceps raising base 201 is provided at the distal end opening 196 of the first channel 191 and is so mounted as to be rotatable about a fixed pin 202 fixed to the distal end block 194. A forceps raising wire 203 is fixedly connected to an end (forceps raising base) opposite to the fixed pin 202. The forceps raising wire 203 is coupled to a traction mechanism provided at the proximal operation section not shown. The traction mechanism is operated by the forceps raising lever, causing the forceps raising wire 203 to be pulled to allow the raising of the forceps raising base 201. By doing so, grasping forceps 205 inserted through the first channel 191 is moved in a direction of an arrow in FIG. 48. When the forceps raising wire 203 is brought back to an original state, then the forceps raising base 201 is set in a lying-down position and the grasping forceps 205 is moved back in a direction of an arrow in FIG. 48.

Further, the distal end opening 197 of the second channel 192 is inclined at an angle of less than 90° relative to the center axis direction of the insertion section 190 on the distal end of the insertion section 190. An electric surgical knife 206 inserted through the second channel 192 is inserted and withdrawn at an angle of less than 90° relative to the center axis direction of the insertion section 190.

Figure 49:
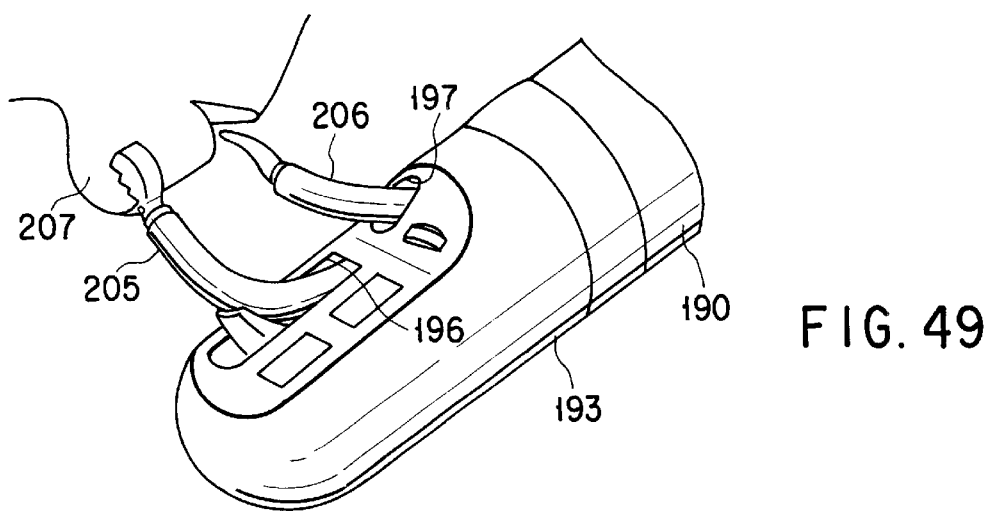
FIG. 49 is an explanatory view showing a situation under which treating operation is performed on a living tissue portion by the treating endoscope.
Figure 50:
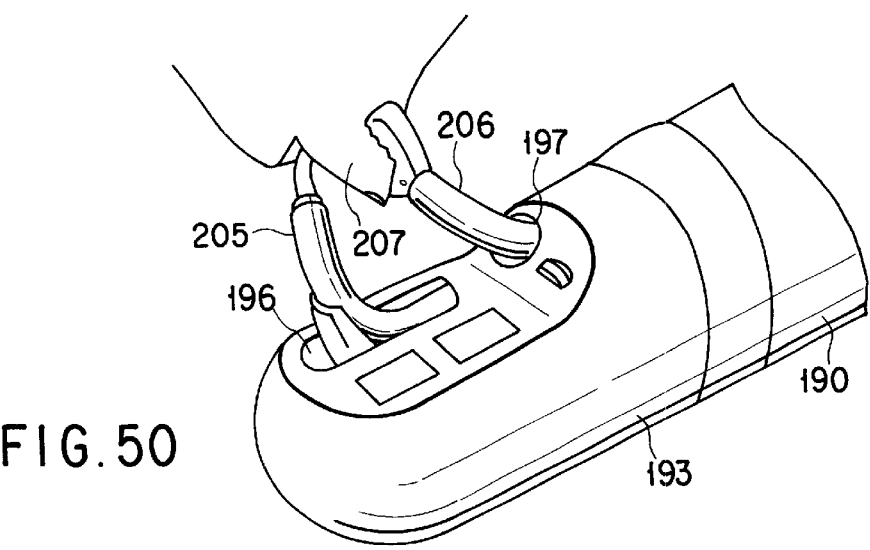
FIG. 50 is an explanatory view showing a situation under which treating operation is performed on the living tissue by the treating endoscope.

FIG. 49 shows a state of use of the endoscope. In this state, a diseased portion is grasped by the grasping forceps 205 projected from the first channel 191 of the endoscope whose insertion section 190 has been inserted into the body cavity. And the diseased portion 207 is cut off by the electric surgical knife 206 projected from the second channel 192. By adjusting a raised state of the grasping forceps 205 the diseased portion is cut opened by the electric surgical knife 206 while applying a tension.

The treating procedure may be done while inserting the grasping forceps 205 from the second channel 192 and the electric surgical knife 206 from the first channel 191. In this case, the electric surgical knife 206 can be approached to a diseased portion on a side opposite to a side on which the endoscope is inserted, that is, on a relatively hard-to-approach side.

By approaching to the diseased portion by the use of the side-viewing type endoscope it is possible to treat a region of interest by front-viewing the region located in a hard-to-front-view position. Since the region of interest is cut off by the forceps while being grasped by the grasping forceps, it is easily possible to cut open a soft living tissue by an electric surgical knife for instance while steadily fastening the tissue in position.

(Section 6 of Another Endoscopic Diagnostic System)

A distal end cap 212 is provided on a distal end section 211 of a side-viewing type endoscope in a treating endoscopic system. The procedure will be explained below with reference to FIGS. 51 to 55.

Figure 51:
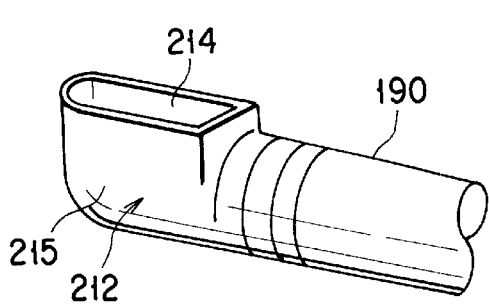
FIG. 51 is a perspective view showing a distal end section of another treating endoscope.
Figure 52:
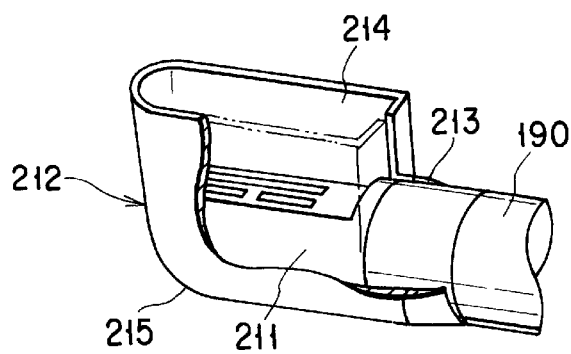
FIG. 52 is a perspective view showing a distal end section of the treating endoscope with a distal end cap shown partly cut away.

FIG. 51 shows the above-mentioned side-viewing type endoscope whose insertion section 190 is equipped with a distal end cap 212. The distal end cap 212 comprises, as shown in FIG. 52, a rubber section 213 for fixing a distal end cap 212 to a rigid section of a distal end section 211 and a transparent cap section 215, such as transparent hard polycarbonate, having an opening 214.

Figure 53:
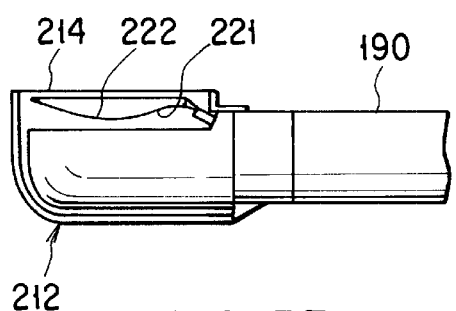
FIG. 53 is an explanatory view showing a situation under which treating operation is performed on a living tissue by the treating endoscope.
Figure 54:
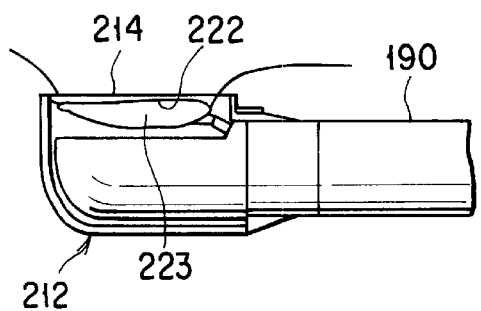
FIG. 54 is an explanatory view showing a situation under which treating operation is performed on the living tissue by the treating endoscope.
Figure 55:
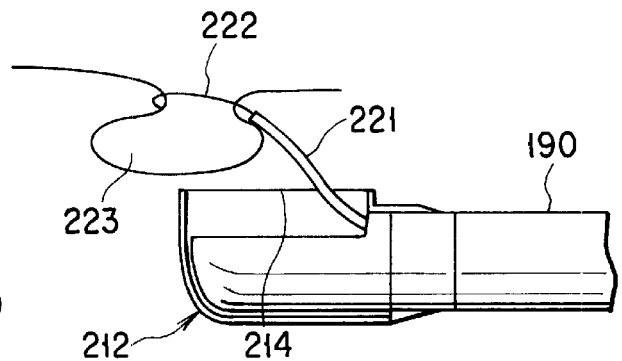
FIG. 55 is an explanatory view showing a situation under which treating operation is performed on the living tissue by the treating endoscope.

FIGS. 53 to 55 show an example of use of an endoscope with a distal cap 212 equipped therewith.

With the insertion section 190 inserted into a body cavity of a patient, a high frequency snare 221 is inserted into a second channel and a snare wire 222 of the high frequency snare 221 is projected via the distal end opening. The snare wire 222 is opened in the distal end cap 212. In this state, the opening 214 of the distal end cap 212 is pushed against a diseased portion 223 and, by applying a suction from the first channel 191 to a tissue portion of the diseased portion 223 to suck it into the distal end cap 212 and pulling back the snare wire with the tissue portion trapped and tightened, it is possible to supply a high frequency current and cut off the diseased portion 223.

According to this system, since this endoscope has a channel with the distal end opening along the channels' axial direction, it is possible to perform treatment with the use of a side-viewing type endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic surgery apparatus for performing treating operation in a body cavity of a patient, comprising:

an endoscope having an insertion section with at least an observation device incorporated therein;

at least first and second treating tools each having an insertion section and each being operable in combination with the endoscope;

a distance adjusting device for adjusting a relative distance between at least one pair of the observation device of the endoscope, insertion section of the first treating tool and insertion section of the second treating tool in a direction substantially orthogonal with an axial direction of the insertion section of the endoscope; and an operating device for remotely operating the distance adjusting device;

wherein the distance adjusting device comprises a treating tool raising device arranged at a distal end portion of the insertion portion of the endoscope for raising one of the treating tools in a direction away from the insertion section of the other one of the first and second treating tools and different from the axial direction of the insertion section of the endoscope.

2. An endoscopic surgery apparatus according to claim 1, wherein at least one of the insertion sections of the first and second treating tools is flexible in nature and parallel with the insertion section of the endoscope.

3. An endoscopic surgery apparatus according to claim 1, further comprising a third treating tool having an insertion section, and wherein the distance adjusting device adjusts a relative distance between at least one pair of the insertion section of the endoscope, the insertion section of the first treating tool, the insertion section of the second treating tool and the insertion section of the third treating tool in a direction substantially orthogonal with the axial direction of the insertion section of the endoscope.

4. An endoscopic surgery apparatus according to claim 1, wherein the insertion section of the endoscope has a first channel through which the first treating tool is inserted and a second channel through which the second treating tool is inserted, and wherein the treating tool raising device raises the insertion section of one of said first and second treating tools in said direction away from the insertion section of the other one of said first and second treating tools and in a direction substantially orthogonal with the axial direction of the insertion section of the endoscope.

5. An endoscopic surgery apparatus according to claim 1, wherein the distance adjusting device comprises a balloon arranged on an outer periphery of the insertion section of the endoscope and between one pair of the treating tools, and wherein the balloon is inflatable by a given amount of fluid supplied thereto and the fluid is dischargeable therefrom through an associated tube.

6. An endoscopic surgery apparatus according to claim 5, wherein the operation device comprises a button on a proximal end section of the endoscope for controlling the supply and discharge of the fluid to and from the balloon.

7. An endoscopic surgery apparatus according to claim 1, wherein the distance adjusting device comprises a plurality of wires provided around an outer periphery of the insertion section of the endoscope which together form a basket-like unit that is expanded and contracted by pushing and pulling of the wires.

8. An endoscopic surgery apparatus according to claim 1, further comprising a first guide tube allowing an insertion of the insertion section of the first treating tool to lead to a given position and a second guide tube allowing an insertion of the insertion section of the second treating tool to lead to a given position, wherein, through operations of the guide tubes, the distance adjusting device adjusts a relative distance between the insertion section of the first treating tool and the insertion section of the second treating tool in a direction substantially orthogonal with the axial direction of the insertion section of the endoscope.

9. An endoscopic surgery apparatus according to claim 8, wherein at least one of the insertion sections of the first and second guide tubes comprises a bending section.

10. An endoscopic surgery apparatus according to claim 1, further comprising a first tube allowing an insertion of the insertion section of the first treating tool to lead to a given position, a second tube allowing an insertion of the insertion section of the second treating tool to lead to a given position and a third tube allowing the insertion section of the endoscope to lead to a given position.

11. An endoscopic surgery apparatus according to claim 10, wherein distal end sections of the first tube, the second tube and the third tube are coupled and bundled together.

12. An endoscopic surgery apparatus according to claim 10, wherein the first and second tubes are arranged outside the third tube on opposite sides thereof, and distal ends of the first and second tubes are externally rearwardly inclined.

13. An endoscopic surgery apparatus according to claim 1, wherein the insertion section of the endoscope has a first channel through which the first treating tool is inserted and a second channel through which the second treating tool is inserted, and wherein the treating tool raising device comprises a base pivoted at a proximal end portion thereof and a wire coupled to a distal end portion of the base.

14. An endoscopic surgery apparatus according to claim 13, wherein the distal end portion of the base is adapted to be raised when the wire coupled thereto is pulled in a proximal direction, thereby raising the insertion section of the second treating tool inserted in the second channel away from the insertion section of the first treating tool inserted in the second channel.

15. An endoscopic surgery apparatus according to claim 13, wherein the base is provided in a recess formed in an inner surface portion situated in a side of the first channel, adjacent to and below the second channel.

16. An endoscopic surgery apparatus according to claim 14, wherein the wire is guided in the proximal direction through a guide tube provided in the insertion section of the endoscope.

* * * * *